US011708421B2

(12) United States Patent
Kedmi et al.

(10) Patent No.: US 11,708,421 B2
(45) Date of Patent: Jul. 25, 2023

(54) MODULAR PLATFORM FOR TARGETED THERAPEUTICS

(71) Applicant: Ramot at Tel-Aviv University Ltd., Tel-Aviv (IL)

(72) Inventors: Ranit Kedmi, Tel-Aviv (IL); Nuphar Veiga, Yakum (IL); Itai Benhar, Rehovot (IL); Dan Peer, Kiryat-Ono (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/316,629

(22) PCT Filed: Jul. 18, 2017

(86) PCT No.: PCT/IB2017/054334
§ 371 (c)(1),
(2) Date: Jan. 10, 2019

(87) PCT Pub. No.: WO2018/015881
PCT Pub. Date: Jan. 25, 2018

(65) Prior Publication Data
US 2019/0309087 A1    Oct. 10, 2019

Related U.S. Application Data

(60) Provisional application No. 62/363,417, filed on Jul. 18, 2016.

(51) Int. Cl.
| C07K 16/30 | (2006.01) |
| A61K 47/54 | (2017.01) |
| A61K 9/127 | (2006.01) |
| C07K 16/28 | (2006.01) |
| C07K 16/42 | (2006.01) |
| C12N 15/11 | (2006.01) |
| A61P 35/00 | (2006.01) |

(52) U.S. Cl.
CPC ............ *C07K 16/30* (2013.01); *A61K 9/127* (2013.01); *A61K 47/543* (2017.08); *A61P 35/00* (2018.01); *C07K 16/2809* (2013.01); *C07K 16/2812* (2013.01); *C07K 16/2815* (2013.01); *C07K 16/2845* (2013.01); *C07K 16/2866* (2013.01); *C07K 16/2896* (2013.01); *C07K 16/4241* (2013.01); *C12N 15/11* (2013.01); *C12N 15/111* (2013.01); *C12N 2320/32* (2013.01)

(58) Field of Classification Search
None
See application file for complete search history.

(56) References Cited

U.S. PATENT DOCUMENTS

| 5,530,101 | A | 6/1996 | Queen et al. |
| 5,814,318 | A | 9/1998 | Lonberg et al. |
| 6,440,736 | B1 * | 8/2002 | Logtenberg ........ C07K 16/2815 435/375 |
| 7,094,571 | B2 * | 8/2006 | Harvey ............... C12N 15/1034 435/7.1 |
| 7,575,871 | B2 | 8/2009 | Griffin et al. |
| 7,611,866 | B2 * | 11/2009 | Georgiou ................ C40B 40/02 435/69.1 |
| 8,067,179 | B2 * | 11/2011 | Georgiou ............. G01N 33/566 536/25.4 |
| 8,535,890 | B2 | 9/2013 | Kashmiri et al. |
| 2004/0058403 | A1 | 3/2004 | Harvey et al. |
| 2013/0064762 | A1 | 3/2013 | Simon |
| 2015/0246135 | A1 | 9/2015 | Kedmi et al. |
| 2020/0101170 | A1 | 4/2020 | Kedmi et al. |

FOREIGN PATENT DOCUMENTS

| EP | 0506124 | 9/1992 | |
| WO | WO 91/07987 | 6/1991 | |
| WO | WO 99/01556 | 1/1999 | |
| WO | WO 2005/060457 | 7/2005 | |
| WO | WO 2006/078987 | 7/2006 | |
| WO | WO 2006/082406 | 8/2006 | |
| WO | WO 2007/127272 | 11/2007 | |
| WO | WO 2008/116149 | 9/2008 | |
| WO | WO 2011/139792 | 11/2011 | |
| WO | WO 2014/041544 | 3/2014 | |
| WO | WO-2014041544 A1 * | 3/2014 | ......... A61K 47/6909 |
| WO | WO 2018/015881 | 1/2018 | |

OTHER PUBLICATIONS

Delgoffe et al., Mol. Immunology 46(13):2694-2698 (Year: 2009).*
De Kruif et al., FEBS Letter 399: 232-236 (Year: 1996).*
Official Action dated Mar. 18, 2019 From the US Patent and Trademark Office Re. U.S. Appl. No. 14/427,711. (7 pages).
Van der Heyde et al. "Analysis of Antigen-Specific Antibodies and Their Isotypes in Experimental Malaria" . Cytometry Part A, The Journal of the International Society for Analytical Cytology, 71(4): 242-250, 2007.
Applicant-Initiated Interview Summary dated Apr. 12, 2018 From the US Patent and Trademark Office Re. U.S. Appl. No. 14/427,711. (3 pages).
International Preliminary Report on Patentability dated Mar. 26, 2015 From the International Bureau of WIPO Re. Application No. PCT/IL2013/050775.
International Preliminary Report on Patentability dated Jan. 31, 2019 From the International Bureau of WIPO Re. Application No. PCT/IB2017/054334. (11 Pages).
International Search Report and the Written Opinion dated Nov. 8, 2017 From the International Searching Authority Re. Application No. PCT/IB2017/054334. (15 Pages).
International Search Report and the Written Opinion dated Feb. 21, 2014 From the International Searching Authority Re. Application No. PCT/IL2013/050775.
Office Action and Search Report dated Mar. 17, 2013 From the Israel Patent Office Re. Application No. 221909.

(Continued)

*Primary Examiner* — Phuong Huynh

(57) ABSTRACT

A lipidated secondary antibody is disclosed. Particles comprising same are also disclosed.

12 Claims, 10 Drawing Sheets
(10 of 10 Drawing Sheet(s) Filed in Color)
Specification includes a Sequence Listing.

(56) References Cited

OTHER PUBLICATIONS

Official Action dated Feb. 8, 2018 From the US Patent and Trademark Office Re. U.S. Appl. No. 14/427,711. (11 pages).
Official Action dated Jul. 19, 2017 From the US Patent and Trademark Office Re. U.S. Appl. No. 14/427,711. (10 pages).
Official Action dated Sep. 20, 2018 From the US Patent and Trademark Office Re. U.S. Appl. No. 14/427,711. (10 pages).
Official Action dated Dec. 30, 2016 From the US Patent and Trademark Office Re. U.S. Appl. No. 14/427,711. (14 pages).
Restriction Official Action dated Sep. 9, 2016 From the US Patent and Trademark Office Re. U.S. Appl. No. 14/427,711.
Ansell et al. "Antibody Conjugation Methods for Active Targeting of Liposomes", Methods in Molecular Medicine: Drug Targeting: Strategies, Principles, and Applications, 25(Chap.4): 51-67, 2000.
Begent et al. "Liposomally Entrapped Second Antibody Improves Tumour Imaging With Radiolabelled (First) Antitumour Antibody", The Lancet, XP055101004, p. 739-742, Oct. 2, 1982. Abstract, p. 739, 741, r-h col.
Braisted et al. "Minimizing a Binding Domain From Protein A", Proc. Natl. Acad. Sci. USA, 93(12): 5688-5692, Jun. 11, 1996.
Choe et al. "Fc-Binding Ligands of Immunoglobulin G: An Overview of High Affinity Proteins and Peptides", Materials, 9(12): 994-1-994-17, Dec. 8, 2016.
De Kruif et al. "Biosynthetically Lipid-Modified Human ScFv Fragments From Phage Display Libraries as Targeting Molecules for Immunoliposomes", FEBS Letters, 399(3): 232-236, Dec. 16, 1996.
Harvey et al. "Anchored Periplasmic Expression, A Versatile Technology for the Isolation of High-Affinity Antibodies From *Escherichia coli*-Expressed Libraries". Proc. Natl. Acad. Sci. USA, PNAS, 101(25): 9193-9198, Jun. 22, 2004. Fig.1.
Jeong et al. "Efficiant Selection of IgG Fc Domain-Binding Peptides Fused to Fluorescent Protein Using *E. Coli* Expression System and Dot-Blotting Assay", Peptides, 31(2): 202-206, Available Online Dec. 16, 2009.
Jones et al. "Blood-Brain Barrier Transport of Therapeutics Via Receptor-Mediation", Pharmaceutical Research, XP019532601, 24(9): 1759-1771, Jul. 10, 2007. Abstract, p. 1767-1769.
Julien et al. "Utilization of Monoclonal Antibody-Targeted Nanomaterials in the Treatment of Cancer", MAbs, 3(5): 467-478, Sep./Oct. 2011.
Krystofiak et al. "Elimination of Tumor Cells Using Folate Receptor Targeing by Antibody-Conjugated, Gold-Coated Magnetite Nanoparticles in a Murine Breast Cancer Model", Journal of Nanomaterials, 2012: Article ID 431012, 9 P., 2012.
Laukkanen et al. "Lipid-Tagged Antibodies: Bacterial Expression and Characterization of A Lipoprotein—Single-Chain Antibody Fusion Protein", Protein Engineering, 6(4): 449-454, 1993.
Leserman et al. "Targeting to Cells of Fluorescent Liposomes Covalently Coupled With Monoclonal Antibody or Protein A", Nature, 288: 602-604, Dec. 11, 1980.
Li et al. "Electrochemical Immunosensors for Cancer Biomarker With Signal Amplification Based on Ferrocene Functionalized Iron Oxide Nanoparticles", Biosensors and Bioelectronics, XP028369905, 26(8): 3590-3595, Feb. 4, 2011. Abstract.
Matthay et al. "Antibody-Directed Liposomes: Comparison of Various Ligands for Association, Endocytosis, and Drug Delivery", Cancer Research, 46: 4904-4910, Oct. 1986.
Owens "Faster, Deeper, Smaller—The Rise of Antibody-Like Scaffolds", Nature Biotechnology, 35(7): 602-603, Jul. 2017.
Pitsillides et al. "Selctive Cell Targeting With Light-Absorbing Microparticles and Nanoparticles", Biophysical Journal, XP002428862, 84(6): 4023-4032, Jun. 1, 2003. p. 4028.
Presta et al. "Humanization of an Antibody Directed Against IgE", The Journal of Immunology, XP002094432, 151(5): 2623-2632, Sep. 1, 1993. Abstract. p. 2624, 2629-2631.
Ritter et al. "Serological Analysis of Human Anti-Hun:1an Antibody Responses in Colon Cancer Patients Treated with Repeated Doses of Humanized 1Vlonodonal Antibody A33", Cancer Research 61:6851-6859, Sep. 15, 2001.
Serda et al. "Quantitative Mechanics of Endothelial Phagocytosis of Silicon Microparticles", Cytometry Part A, XP008111439, 75(9): 752-760, Sep. 1, 2009. p. 757, r-h col.
Torchilin "Fluorescence Microscopy to Follow the Targetin of Liposomes and Micelles to Cells and Their Intracellular Fate", Advanced Drug Delivery Reviews, XP027771274, 57(1): 95-109, Jan. 2, 2005. Abstract, p. 96, Line 97.
Torchilin et al. "P-Nitrophenylcarbonyl-PEG-PE-Liposomes: Fast and Simple Attachment of Specific Ligands, Including Monoclonal Antibodies, to Distal Ends of PEG Chains Via P-Nitrophenylcarbonyl Groups", Biochimica et Biophysica Acta, XP002257432, 1511(2): 397-411, Apr. 2. p. 404.
Ugelstad et al. "Biomedical Applications of Monodisperse Magnetic Polymer Particles", Nato Advanced Science Institute, XP000603237, p. 355-370, Jan. 1, 1987. p. 361.
Vazquez-Lombardi et al. "Challenges and Opportunities for Non-Antibody Scaffold Drugs", Drug Discovery Today, 20(10): 1271-1283, Oct. 2015.
Wu et al. "Immunofluorescence Labeling of Cancer Marker Her2 and Other Cellular Targets With Semiconductor Quantum Dots", Nature Biotechnology, 21: 41-46, Jan. 2003.
Supplementary European Search Report and the European Search Opinion dated Mar. 12, 2020 From the European Patent Office Re. Application No. 17830577.7. (9 Pages).
Ben-Arie et al. "Integrin-Targeted Nanoparticles for siRNA Delivery". Integrin and Cell Adhesion Molecules: Methods and Protocols, Methods in Molecular Biology, XP055136709, 757(Chap.29): 497-507, Published Online Jun. 8, 2011.
Kedmi et al. "A Modular Platform for Targeted RNAi Therapeutics", Nature Nanotechnology. XP036449126, 13(3): 214-219, Published Online Jan. 29, 2018.

* cited by examiner

FIG. 2A
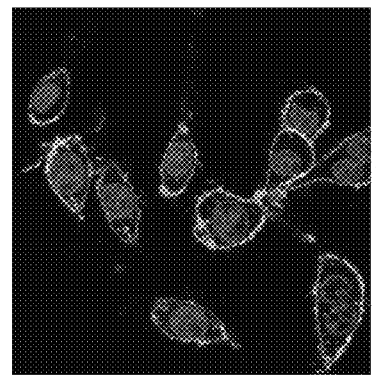
FIG. 2B
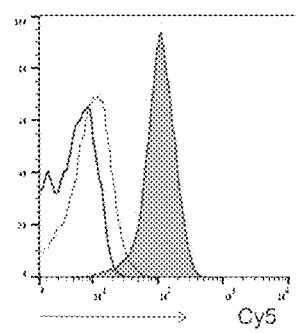
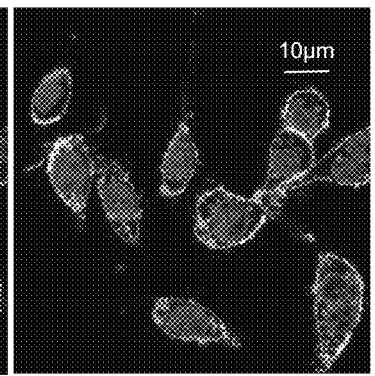
FIG. 2C

FIG. 4A
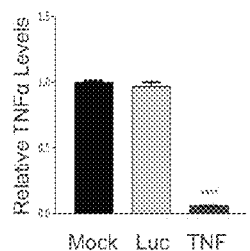
FIG. 4B
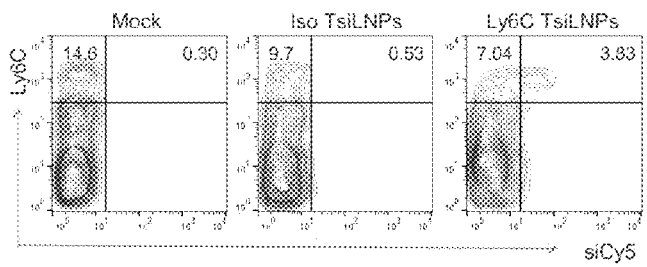
FIG. 4C
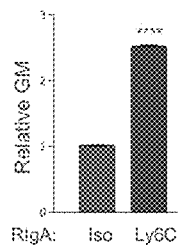
FIG. 4D
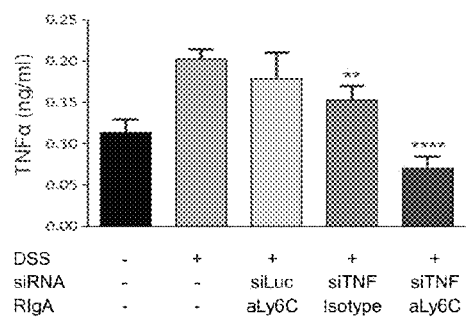
FIG. 4E
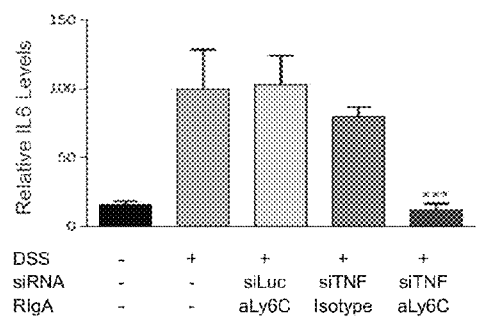
FIG. 4F
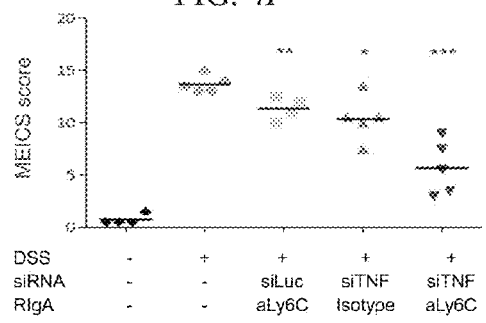
FIG. 4G
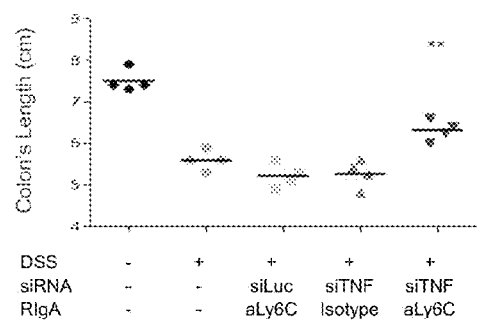
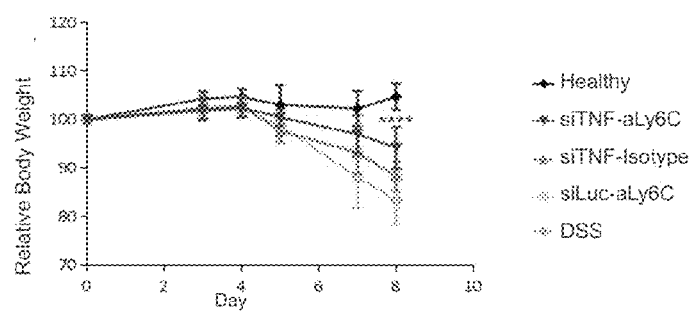
FIG. 4H FIG. 6A
FIG. 6B
FIG. 6C
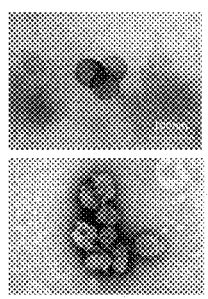
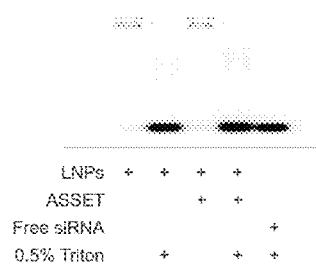
LNPs
ASSET
Free siRNA
0.5% Triton
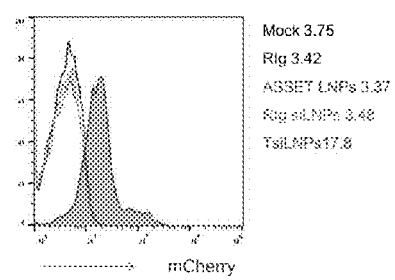
Mock 3.75
Rig 3.42
ASSET LNPs 3.37
Rig siLNPs 3.48
TsiLNPs 17.8
mCherry
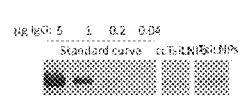
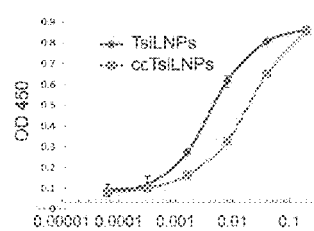
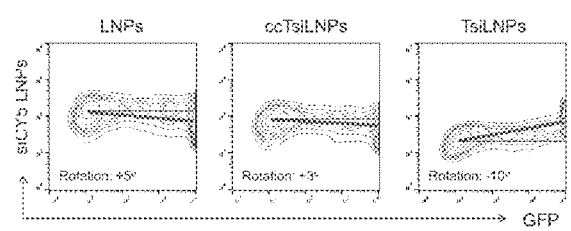
FIG. 6D
FIG. 6E
FIG. 6F

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: CD45 sense SiRNA sequence
<220> FEATURE:
<221> NAME/KEY: misc_feature
<222> LOCATION: (1)..(2)
<223> OTHER INFORMATION: 2'-OMe-modified nucleotides
<220> FEATURE:
<221> NAME/KEY: misc_feature
<222> LOCATION: (5)..(6)
<223> OTHER INFORMATION: 2'-OMe-modified nucleotides
<220> FEATURE:
<221> NAME/KEY: misc_feature
```

<222> LOCATION: (10)..(13)
<223> OTHER INFORMATION: 2'-OMe-modified nucleotides
<220> FEATURE:
<221> NAME/KEY: misc_feature
<222> LOCATION: (18)..(18)
<223> OTHER INFORMATION: 2'-OMe-modified nucleotides
<220> FEATURE:
<221> NAME/KEY: misc_feature
<222> LOCATION: (20)..(21)
<223> OTHER INFORMATION: deoxyribonucleotide
<220> FEATURE:
<221> NAME/KEY: misc_feature
<222> LOCATION: (20)..(21)
<223> OTHER INFORMATION: phosphorothioate linkages

<400> SEQUENCE: 1
cuggcugaau uucagagcat t                                              21

<210> SEQ ID NO 2
<211> LENGTH: 21
<212> TYPE: DNA
<213> ORGANISM: Artificial sequence
<220> FEATURE:
<223> OTHER INFORMATION: CD45 anti-sense SiRNA sequence
<220> FEATURE:
<221> NAME/KEY: misc_feature
<222> LOCATION: (13)..(13)
<223> OTHER INFORMATION: 2'-OMe-modified nucleotides
<220> FEATURE:
<221> NAME/KEY: misc_feature
<222> LOCATION: (16)..(16)
<223> OTHER INFORMATION: 2'-OMe-modified nucleotides
<220> FEATURE:
<221> NAME/KEY: misc_feature
<222> LOCATION: (20)..(21)
<223> OTHER INFORMATION: deoxyribonucleotide
<220> FEATURE:
<221> NAME/KEY: misc_feature
<222> LOCATION: (20)..(21)
<223> OTHER INFORMATION: phosphorothioate linkages

<400> SEQUENCE: 2
ugcucugaaa uucagccagt t                                              21

<210> SEQ ID NO 3
<211> LENGTH: 21
<212> TYPE: DNA
<213> ORGANISM: Artificial sequence
<220> FEATURE:
<223> OTHER INFORMATION: Luc sense SiRNA sequence
<220> FEATURE:
<221> NAME/KEY: misc_feature
<222> LOCATION: (1)..(3)
<223> OTHER INFORMATION: 2'-OMe-modified nucleotides
<220> FEATURE:
<221> NAME/KEY: misc_feature
<222> LOCATION: (5)..(5)
<223> OTHER INFORMATION: 2'-OMe-modified nucleotides
<220> FEATURE:
<221> NAME/KEY: misc_feature
<222> LOCATION: (7)..(8)
<223> OTHER INFORMATION: 2'-OMe-modified nucleotides
<220> FEATURE:
<221> NAME/KEY: misc_feature
<222> LOCATION: (12)..(12)
<223> OTHER INFORMATION: 2'-OMe-modified nucleotides
<220> FEATURE:
<221> NAME/KEY: misc_feature
<222> LOCATION: (14)..(17)
<223> OTHER INFORMATION: 2'-OMe-modified nucleotides
<220> FEATURE:
<221> NAME/KEY: misc_feature
<222> LOCATION: (20)..(21)
<223> OTHER INFORMATION: deoxyribonucleotide
<220> FEATURE:

-continued

```
<221> NAME/KEY: misc_feature
<222> LOCATION: (20)..(21)
<223> OTHER INFORMATION: phosphorothioate linkages

<400> SEQUENCE: 3
cuuacgcuga guacuucgat t                                              21

<210> SEQ ID NO 4
<211> LENGTH: 21
<212> TYPE: DNA
<213> ORGANISM: Artificial sequence
<220> FEATURE:
<223> OTHER INFORMATION: Luc anti-sense  SiRNA sequence
<220> FEATURE:
<221> NAME/KEY: misc_feature
<222> LOCATION: (7)..(7)
<223> OTHER INFORMATION: 2'-OMe-modified nucleotides
<220> FEATURE:
<221> NAME/KEY: misc_feature
<222> LOCATION: (11)..(11)
<223> OTHER INFORMATION: 2'-OMe-modified nucleotides
<220> FEATURE:
<221> NAME/KEY: misc_feature
<222> LOCATION: (16)..(16)
<223> OTHER INFORMATION: 2'-OMe-modified nucleotides
<220> FEATURE:
<221> NAME/KEY: misc_feature
<222> LOCATION: (20)..(21)
<223> OTHER INFORMATION: deoxyribonucleotide
<220> FEATURE:
<221> NAME/KEY: misc_feature
<222> LOCATION: (20)..(21)
<223> OTHER INFORMATION: phosphorothioate linkages

<400> SEQUENCE: 4
ucgaaguacu cagcguaagt t                                              21

<210> SEQ ID NO 5
<211> LENGTH: 25
<212> TYPE: DNA
<213> ORGANISM: Artificial sequence
<220> FEATURE:
<223> OTHER INFORMATION: TNF alpha sense SiRNA sequence
<220> FEATURE:
<221> NAME/KEY: misc_feature
<222> LOCATION: (1)..(2)
<223> OTHER INFORMATION: 2'-OMe-modified nucleotides
<220> FEATURE:
<221> NAME/KEY: misc_feature
<222> LOCATION: (4)..(4)
<223> OTHER INFORMATION: 2'-OMe-modified nucleotides
<220> FEATURE:
<221> NAME/KEY: misc_feature
<222> LOCATION: (6)..(6)
<223> OTHER INFORMATION: 2'-OMe-modified nucleotides
<220> FEATURE:
<221> NAME/KEY: misc_feature
<222> LOCATION: (12)..(12)
<223> OTHER INFORMATION: 2'-OMe-modified nucleotides
<220> FEATURE:
<221> NAME/KEY: misc_feature
<222> LOCATION: (14)..(14)
<223> OTHER INFORMATION: 2'-OMe-modified nucleotides
<220> FEATURE:
<221> NAME/KEY: misc_feature
<222> LOCATION: (16)..(16)
<223> OTHER INFORMATION: 2'-OMe-modified nucleotides
<220> FEATURE:
<221> NAME/KEY: misc_feature
<222> LOCATION: (18)..(18)
<223> OTHER INFORMATION: 2'-OMe-modified nucleotides

<400> SEQUENCE: 5
gucucagccu cuucucauuc cugct                                          25
```

<210> SEQ ID NO 6
<211> LENGTH: 27
<212> TYPE: DNA
<213> ORGANISM: Artificial sequence
<220> FEATURE:
<223> OTHER INFORMATION: TNF alpha anti-sense SiRNA sequence
<220> FEATURE:
<221> NAME/KEY: misc_feature
<222> LOCATION: (3)..(3)
<223> OTHER INFORMATION: 2'-OMe-modified nucleotides
<220> FEATURE:
<221> NAME/KEY: misc_feature
<222> LOCATION: (9)..(9)
<223> OTHER INFORMATION: 2'-OMe-modified nucleotides
<220> FEATURE:
<221> NAME/KEY: misc_feature
<222> LOCATION: (11)..(11)
<223> OTHER INFORMATION: 2'-OMe-modified nucleotides
<220> FEATURE:
<221> NAME/KEY: misc_feature
<222> LOCATION: (13)..(13)
<223> OTHER INFORMATION: 2'-OMe-modified nucleotides
<220> FEATURE:
<221> NAME/KEY: misc_feature
<222> LOCATION: (23)..(23)
<223> OTHER INFORMATION: 2'-OMe-modified nucleotides
<220> FEATURE:
<221> NAME/KEY: misc_feature
<222> LOCATION: (25)..(27)
<223> OTHER INFORMATION: 2'-OMe-modified nucleotides

<400> SEQUENCE: 6
agcaggaaug agaagaggcu gagacau                              27

<210> SEQ ID NO 7
<211> LENGTH: 25
<212> TYPE: DNA
<213> ORGANISM: Artificial sequence
<220> FEATURE:
<223> OTHER INFORMATION: PLK1 sense  SiRNA sequence
<220> FEATURE:
<221> NAME/KEY: misc_feature
<222> LOCATION: (1)..(2)
<223> OTHER INFORMATION: 2'-OMe-modified nucleotides
<220> FEATURE:
<221> NAME/KEY: misc_feature
<222> LOCATION: (4)..(4)
<223> OTHER INFORMATION: 2'-OMe-modified nucleotides
<220> FEATURE:
<221> NAME/KEY: misc_feature
<222> LOCATION: (6)..(6)
<223> OTHER INFORMATION: 2'-OMe-modified nucleotides
<220> FEATURE:
<221> NAME/KEY: misc_feature
<222> LOCATION: (12)..(12)
<223> OTHER INFORMATION: 2'-OMe-modified nucleotides
<220> FEATURE:
<221> NAME/KEY: misc_feature
<222> LOCATION: (14)..(14)
<223> OTHER INFORMATION: 2'-OMe-modified nucleotides
<220> FEATURE:
<221> NAME/KEY: misc_feature
<222> LOCATION: (16)..(16)
<223> OTHER INFORMATION: 2'-OMe-modified nucleotides
<220> FEATURE:
<221> NAME/KEY: misc_feature
<222> LOCATION: (18)..(18)
<223> OTHER INFORMATION: 2'-OMe-modified nucleotides
<220> FEATURE:
<221> NAME/KEY: misc_feature
<222> LOCATION: (24)..(24)
<223> OTHER INFORMATION: 2'-OMe-modified nucleotides

<400> SEQUENCE: 7
gcuuaaugac gaguucuuua cuuct                                              25

<210> SEQ ID NO 8
<211> LENGTH: 27
<212> TYPE: DNA
<213> ORGANISM: Artificial sequence
<220> FEATURE:
<223> OTHER INFORMATION: PLK1 anti-sense SiRNA sequence
<220> FEATURE:
<221> NAME/KEY: misc_feature
<222> LOCATION: (3)..(3)
<223> OTHER INFORMATION: 2'-OMe-modified nucleotides
<220> FEATURE:
<221> NAME/KEY: misc_feature
<222> LOCATION: (9)..(9)
<223> OTHER INFORMATION: 2'-OMe-modified nucleotides
<220> FEATURE:
<221> NAME/KEY: misc_feature
<222> LOCATION: (11)..(11)
<223> OTHER INFORMATION: 2'-OMe-modified nucleotides
<220> FEATURE:
<221> NAME/KEY: misc_feature
<222> LOCATION: (13)..(13)
<223> OTHER INFORMATION: 2'-OMe-modified nucleotides
<220> FEATURE:
<221> NAME/KEY: misc_feature
<222> LOCATION: (23)..(23)
<223> OTHER INFORMATION: 2'-OMe-modified nucleotides
<220> FEATURE:
<221> NAME/KEY: misc_feature
<222> LOCATION: (25)..(27)
<223> OTHER INFORMATION: 2'-OMe-modified nucleotides

<400> SEQUENCE: 8
agaaguaaag aacucgucau uaagcag                                           27

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
ttgtggaagg gctcatgacc                                                   20

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
tcttctgggt ggcagtgatg                                                   20

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
gcaccaccat caaggactca a                                                 21

<210> SEQ ID NO 12
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 12
tcgaggctcc agtgaattcg                                                  20

<210> SEQ ID NO 13
<211> LENGTH: 6
<212> TYPE: PRT
<213> ORGANISM: Artificial sequence
<220> FEATURE:
<223> OTHER INFORMATION: first six amino acid of NlpA can be used as an
      N terminal anchor

<400> SEQUENCE: 13

Cys Asp Gln Ser Ser Ser
1               5

<210> SEQ ID NO 14
<211> LENGTH: 117
<212> TYPE: PRT
<213> ORGANISM: Artificial sequence
<220> FEATURE:
<223> OTHER INFORMATION: VH domain of the antibody

<400> SEQUENCE: 14

Glu Val Gln Leu Leu Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Glu Lys Ser Leu Glu Trp Ile
        35                  40                  45

Gly Tyr Ile Asn Pro Tyr Ser Gly Asp Thr Ile Tyr Asn His Lys Phe
    50                  55                  60

Lys Asp Lys Ala Thr Leu Thr Val Tyr Lys Ser Ser Asn Ile Ala Tyr
65                  70                  75                  80

Met Glu Leu Arg Ser Leu Thr Ser Glu Asp Thr Ala Val Tyr Tyr Cys
                85                  90                  95

Ala Arg Gly Gly Tyr Asp Tyr Gly Asp His Trp Gly Gln Gly Thr Thr
            100                 105                 110

Leu Thr Val Ser Ser
        115

<210> SEQ ID NO 15
<211> LENGTH: 107
<212> TYPE: PRT
<213> ORGANISM: Artificial sequence
<220> FEATURE:
<223> OTHER INFORMATION: amino acid sequence of the VL domain (kappa) of
      the antibody

<400> SEQUENCE: 15

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
```

-continued

```
                65                  70                  75                  80
Glu Asp Met Gly Ile Tyr Tyr Cys Leu Gln Asp Asp Glu Phe Pro Arg
                        85                  90                  95
Thr Phe Gly Gly Gly Thr Lys Leu Glu Ile Lys
                100                 105

<210> SEQ ID NO 16
<211> LENGTH: 18
<212> TYPE: PRT
<213> ORGANISM: Artificial sequence
<220> FEATURE:
<223> OTHER INFORMATION: linker sequence of the antibody

<400> SEQUENCE: 16

Gly Ser Ala Gly Gly Gly Gly Ser Gly Gly Gly Gly Ser Gly Gly Gly
1               5                   10                  15

Gly Ser

<210> SEQ ID NO 17
<211> LENGTH: 6
<212> TYPE: PRT
<213> ORGANISM: Artificial sequence
<220> FEATURE:
<223> OTHER INFORMATION: short peptide

<400> SEQUENCE: 17

Cys Asp Asn Ser Ser Ser
1               5

<210> SEQ ID NO 18
<211> LENGTH: 15
<212> TYPE: PRT
<213> ORGANISM: Artificial sequence
<220> FEATURE:
<223> OTHER INFORMATION: Biotin lygase tag

<400> SEQUENCE: 18

Leu His His Ile Leu Asp Ala Gln Lys Met Val Trp Asn His Arg
1               5                   10                  15
```

MODULAR PLATFORM FOR TARGETED THERAPEUTICS

RELATED APPLICATIONS

This application is a National Phase of PCT Patent Application No. PCT/IB2017/054334 having International filing date of Jul. 18, 2017, which claims the benefit of priority under 35 USC § 119(e) of U.S. Provisional Patent Application No. 62/363,417 filed on Jul. 18, 2016. The contents of the above applications are all incorporated by reference as if fully set forth herein in their entirety.

SEQUENCE LISTING STATEMENT

The ASCII file, entitled 76332SequenceListing.txt, created on Jan. 10, 2019, comprising 9,954 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates immunoparticles and methods of generating and using same.

Since the discovery of the role of RNA interference (RNAi) in inhibiting gene expression, there is increasing enthusiasm for developing small interfering (si)RNA-based therapeutics to knock down disease-causing genes. Clinical studies using lipid based nanoparticles (LNPs) that carry siRNA payloads or GalNAc-conjugated siRNAs that are taken up by the asialoglycoprotein receptor on hepatocytes are showing impressive and durable gene knockdown in the liver in advance phase trials with little toxicity. However, designing clinically useful strategies for delivering siRNAs to tissues outside the liver has proven difficult. Most LNPs get trapped in the liver and other siRNA conjugates have so far not worked well. A flexible platform for cell-specific siRNA uptake would be ideal. Targeted uptake to the diseased tissue would have the advantage of reduced bystander cell toxicity and require lower drug doses. The wide availability of monoclonal antibodies that bind with high affinity and selectivity to virtually any cell-specific receptor make them desirable components of a targeted delivery platform that could potentially be used to deliver siRNAs or other macromolecules to a wide range of cell types. Although antibody-mediated delivery and gene knockdown has been demonstrated for specific cell types using antibody fusion proteins and conjugated LNPs in animal models, these methods require a lot of optimization for each cell type (1-5). A flexible platform that can be nimbly applied to target multiple tissues by substituting one antibody for another has so far not been possible because conventional methods of chemical conjugation to antibodies for constructing targeting delivery systems are inefficient and require careful optimization for each targeted carrier for functionality.

Background art includes US Patent Application No. 20070099267 and WO 2014/041544.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

SUMMARY OF THE INVENTION

According to one aspect of the present invention there is provided a lipidated secondary antibody.

According to one aspect of the present invention there is provided an isolated polynucleotide encoding the lipidated secondary antibody described herein.

According to one aspect of the present invention there is provided a cell expressing the isolated polynucleotide described herein.

According to one aspect of the present invention there is provided a pharmaceutical composition comprising a lipidated polypeptide immunocomplexed with a primary antibody, wherein the secondary antibody is non-covalently attached to an outer surface of a particle via the lipidated portion of the lipidated secondary antibody and wherein the particle is loaded with a pharmaceutical agent.

According to one aspect of the present invention there is provided a method of delivering a pharmaceutical agent to a subject in need thereof, the method comprising administering to the subject the pharmaceutical composition described herein, thereby delivering the pharmaceutical agent to the subject.

According to one aspect of the present invention there is provided an immunoparticle comprising a lipidated polypeptide non-covalently attached to an outer surface of a particle via the lipidated portion of the lipidated polypeptide.

According to one aspect of the present invention there is provided a universal kit for in-vivo delivery of a pharmaceutical agent, the kit comprising the immunoparticle described herein and instructions for effecting immunocomplexation of the lipidated polypeptide to a primary antibody.

According to further features in the described preferred embodiments, the secondary antibody is attached to a lipidated peptide.

According to still further features in the described preferred embodiments the lipidated secondary antibody comprises the sequence as set forth in SEQ ID NO: 13.

According to still further features in the described preferred embodiments, the secondary antibody is a monoclonal antibody.

According to still further features in the described preferred embodiments, the N terminus of the secondary antibody is lipidated.

According to still further features in the described preferred embodiments, the lipidated secondary antibody further comprises a detectable moiety.

According to still further features in the described preferred embodiments, the lipidated secondary antibody further comprises an affinity tag.

According to still further features in the described preferred embodiments, the monoclonal secondary antibody is a humanized monoclonal secondary antibody.

According to still further features in the described preferred embodiments, the lipidated secondary antibody comprises an antigen recognition domain capable of specifically binding a humanized or human primary antibody.

According to still further features in the described preferred embodiments, the cell is a bacterial cell.

According to still further features in the described preferred embodiments, the lipidated polypeptide is the lipidated secondary antibody described herein.

According to still further features in the described preferred embodiments, the lipidated polypeptide is protein A or protein G.

According to still further features in the described preferred embodiments, the lipidated polypeptide is the lipidated secondary antibody described herein.

According to still further features in the described preferred embodiments, the lipidated polypeptide is Protein A or Protein G.

According to still further features in the described preferred embodiments, the polypeptide is immunocomplexed with a humanized or human primary antibody.

According to still further features in the described preferred embodiments, the immunoparticle is loaded with a pharmaceutical agent.

According to still further features in the described preferred embodiments, the pharmaceutical agent is a diagnostic agent.

According to still further features in the described preferred embodiments, the pharmaceutical agent is a therapeutic agent.

According to still further features in the described preferred embodiments, the therapeutic agent is a polynucleotide agent.

According to still further features in the described preferred embodiments, the administering is systemically administering.

According to still further features in the described preferred embodiments, the primary antibody comprises an Fc region.

According to still further features in the described preferred embodiments, the secondary antibody is an antibody fragment and optionally wherein the fragment is selected from the group consisting of a Fab, F(ab)$_2$ an ScFv and a sdFv.

According to still further features in the described preferred embodiments, the primary antibody and the secondary antibody are of different antibody classes or antibody isotypes.

According to still further features in the described preferred embodiments, the primary antibody and the secondary antibody are selected from the group consisting of IgG1, IgG2 and IgG4.

According to still further features in the described preferred embodiments, the primary antibody is an IgG1 and the secondary antibody is an IgG2 or IgG4.

According to still further features in the described preferred embodiments, the primary antibody is selected from the group consisting of anti-CD44, anti-CD34, anti-Ly6C, anti-CD3, anti-CD4, anti-CD25 and anti-intergrin beta 7.

According to still further features in the described preferred embodiments, the primary antibody comprises a plurality of primary antibodies which bind distinct targets.

According to still further features in the described preferred embodiments, the primary antibody comprises an antigen recognition region which binds a tissue specific antigen.

According to still further features in the described preferred embodiments, the primary antibody comprises an antigen recognition region which binds a cancer specific antigen.

According to still further features in the described preferred embodiments, the particle is selected from the group consisting of a polymeric particle, a microcapsule, a liposome, a microsphere, a microemulsion, a nanoparticle, a nanocapsule, a nanosphere and a nanocage.

According to still further features in the described preferred embodiments, the particle comprises a charged external surface.

According to still further features in the described preferred embodiments, the particle comprises a neutral external surface.

According to still further features in the described preferred embodiments, the particle is lipid-based particle.

According to still further features in the described preferred embodiments, the lipids of the lipid based particle comprise cationic lipids.

According to still further features in the described preferred embodiments, the cationic lipid is selected from the group consisting of 1,2-Dilauroyl-sn-Glicero-3-Phosphoethanolamine (DLPE) and 1,2-Dilauroyl-sn-Glicero-3-Glycerol (DLPG), dioleoyl-1,2-diacyl-3-trimethylammonium-propane (DOTAP, at 18:1; 14:0; 16:0, 18:0) and N-[1-(2,3-dioleyloxy)propyl]-N,N,N-trimethlylammonium chloride (DOTMA); dimethyldioctadecylammonium (DDAB); 1,2-dilauroyl-sn-glycero-3-ethylphosphocholine (Ethyl PC, at 12:0; 14:0; 16:0; 18:0; 18:1; 16:0-18:1); 1,2-di-(9Z-octadecenoyl)-3-dimethylammonium-propane and 3ß-[N—(N',N'-dimethylaminoethane)-carbamoyl]cholesterol hydrochloride (DC-Cholesterol).

According to still further features in the described preferred embodiments, the lipids comprise a neutral lipid.

According to still further features in the described preferred embodiments, the neutral lipid comprises phosphatidylethanolamine or dioleilphosphatidylethanolamine (DOPE).

According to still further features in the described preferred embodiments, the lipids comprise anionic phospholipids.

According to still further features in the described preferred embodiments, the anionic phospholipids are selected from the group consisting of phosphatidylserine, phosphatidic acid, phosphatidylcholine and phosphatidyl glycerol.

According to still further features in the described preferred embodiments, the lipidated portion of the secondary antibody comprises the first two amino acids encoded by the E. coli NlpA gene or the first six amino acids encoded by the E. coli NlpA gene.

According to still further features in the described preferred embodiments, the sequence is an inner membrane lipoprotein or fragment thereof selected from the group consisting of: AraH, MglC, MalF, MalG, Mal C, MalD, RbsC, RbsC, ArtM, ArtQ, GliP, ProW, HisM, HisQ, LivH, LivM, LivA, Liv E, Dpp B, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, PhnM, LacY, SecY, TolC, Dsb, B, DsbD, TonB, TatC, CheY, TraB, Exb D, ExbB and Aas.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-E: TsiLNPs assembly and characterization. Characteristics of TsiLNPs composition by western blot after LNPs purification with dialysis (1MDa). ASSET was detected with aHis followed by anti-mouse HRP and RIg was detected with HRP-conjugated secondary anti-Rat antibody (A). Representative histograms demonstrating siCy5 loaded anti LFA-1 (aLFA-1) TsiLNPs binding (blue) over ASSET LNPs (gray) and mock (black) to TK1 cells (B). Confocal microscopy visualization of binding and internalization to RAW 264.7 cells of aCD44 or aCD34 TsiLNPs loaded with siCy5 (red). ASSET was viewed by mCherry (red) fluorescence. Nuclei and membrane were detected using Hoechst 33342 and aCD45 (green fluorescence), respectively (C). ASSET:RIg ratio optimization for TsiLNPs construction. ASSET siLNPs loaded with siCy5 were assembled with various aLFA1 RIg and tested for their uptake by TK1 cells. Binding was assessed via Flow Cytometry and is shown as the difference in GMFI (geometric mean fluorescence intensity) of Cy5. The circles size represents Cy5 standard deviation (D). TsiLNPs, chemically conjugated TsiLNPs (ccTsiLNPs) and siLNPs interaction to transiently express rat Fc receptors on HEK293T cells. HEK293T cells were co transfected with rat fc receptor and GFP reporter. Binding of siCy5 loaded LNPs was assessed and presented as the ratio of LNPs interaction with GFP$^{high}$ cells and GFP$^-$ cells. Data presented as mean±SD, n=3, ****p<0.0001 (E).

FIGS. 4A-I: TsiLNPs mediated therapeutic gene silencing in a DSS induced colitis mouse model. qPCR was used to assess the TNFα expression levels after treatment of activated RAW 264.7 cells with siTNF or siLuc loaded siLNPs. GAPDH served as an endogenous control. Data are presented as mean±SD, n=2, **p<0.0001 (A). siCy5 loaded TsiLNPs assembled with αLy6C, or an isotype control RIg were injected to DSS treated mice. After 1 h blood was collected and targeting to circulating Ly6C+ cells was evaluated by flow cytometry; representative contour blots of live mononuclear-gated cells (B) and bar graphs of Ly6C+-gated cells (C) are presented. Data are presented as mean±SD, n=3, p<0.0001. DSS treated mice were injected intravenously with αLy6C TsiLNPs or isotype control TsiLNPs encapsulating siRNA against TNFα or Luciferase as a control. Colon's TNFα (D) and IL-6 (E) levels were evaluated from a whole tissue lysate by an ELISA assay. Data are presented as mean±SD, n=5, p<0.01, **p<0.0001. MEICS (murine endoscopic index of colitis) was used to score colitis severity (F). Mice bodyweight (Data presented as mean±SD, n=5, **p<0.0001) (H), colon length (G) was measured. *p<0.05, p<0.01, **p<0.0001. Representative images of colon's morphology that was observed by colonoscopy and Representative histology at day 8 (hematoxylin and eosin staining) (I).

FIGS. 6A-F: TsiLNPs characterization. TEM microscopy images of LNPs before and after ASSET incorporation (A). Agarose gel electrophoresis presenting siRNA migration from triton-permeabilized or intact LNPs before and after ASSET assembly (B). Representative histograms demonstrating aLFA-1 TsiLNPs binding to Tk1 cells (bourdeaux). Detection was carried out by measuring ASSET mCherry fluorescence. For controls (gray scale) we used: RIg alone (aLFA-1), ASSET LNPs in the absence of RIg and RIg with siLNPs in the absence of ASSET (C). Representative acrylamide gel quantifying RIg amounts in TsiLNPs and ccTsiLNP along with free RIg serial dilutions (D). αCD34 RIg held by TsiLNPs or ccTsiLNPs apparent affinity to recombinant CD34 evaluated by ELISA (E). HEK293T cells were co transfected with Rat Fc receptor and GFP reporter. Representative contour plots presenting the slope of LNPs binding to transfected vs. not transfected cells as indicator for Fc receptor interactions (F).

DETAILED DESCRIPTION OF SPECIFIC EMBODIMENTS OF THE INVENTION

The present invention, in some embodiments thereof, relates to immunoparticles and methods of generating and using same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Utilizing monoclonal antibodies (mAbs) for targeted delivery of small interfering (si)RNAs has been recently shown to facilitate specific gene silencing in a desired cell population. However, clinical translation of targeted siRNAs has not occurred, in part because of high development and production costs.

The present inventors have conceived of a modular platform to target specific cell types that enables the development of a theoretically unlimited repertoire of targeted delivery carriers. siRNA-loaded lipid nanoparticles (LNP) are coated with oriented, targeting antibodies which are non-covalently bound to a membrane-anchored lipoprotein that recognizes their Fc domain. Unlike chemically conjugated antibodies, these oriented antibodies maintain their high affinity and the LNPs avoid scavenging by Fc receptors on macrophages. Notably, each mAb can be utilized for targeting with almost no need for calibration or optimization.

Figure 3A:
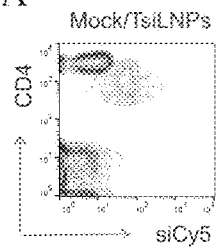
FIGS. 3A-D. TsiLNPs assembled with aCD4 RIg obtained specific uptake and silencing in vivo. C57BL/6 mice were injected intravenously with αCD4 TsiLNPs (siCy5). 1.5 h after administration, blood cells were collected and stained with αCD4 PE (A). αCD4 TsiLNPs loaded with siCD45 or siLuc were injected intravenously on day 1 and 3. CD4+ lymphocytes from inguinal lymph nodes were stained with αCD45 and αCD4 PE. Representative dot blots (from 3 independent experiments) showing the fraction of silenced CD4+ cells (B). Silenced and mock CD4 population is depicted as relative geometric mean intensity (GMFI). Data are presented as mean±SD, n=3, ***p <0.001 (C). RIg-asLNPs targeting complex versatility was demonstrated by administration of siCy5 labeled TsiLNPs that were assembled to 4 different RIg primary antibodies (αITGB7, αCD3, αCD4 and αCD25). Isolated blood leukocytes were detected and distinguished using the following antibodies: αCD4PE, αCD3PerCp, αCD8FITC and αCD25FITC. Representative histograms displayed the specific binding of TsiLNPs to each population (D).
Figure 3B:
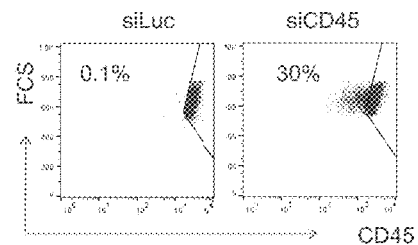
Figure 3C:
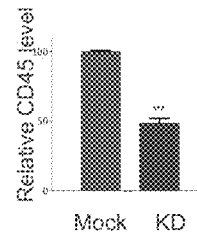
Figure 3D:
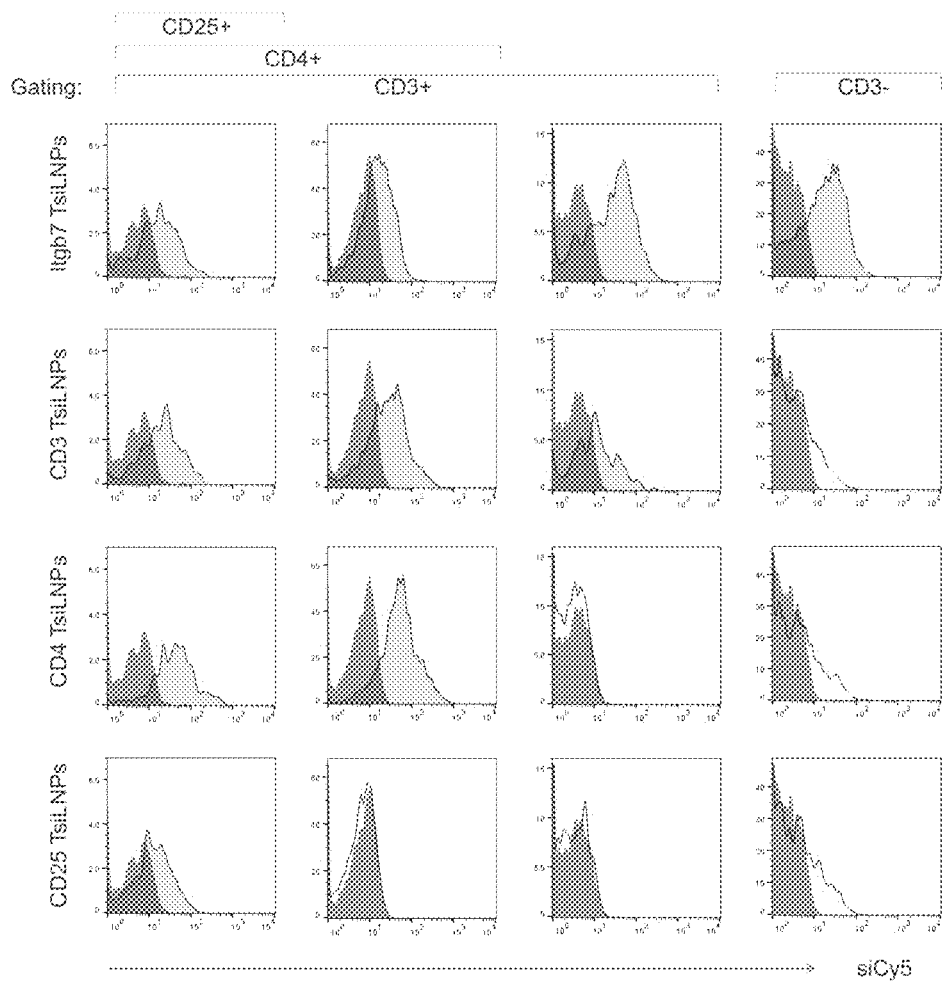
Figure 7A:
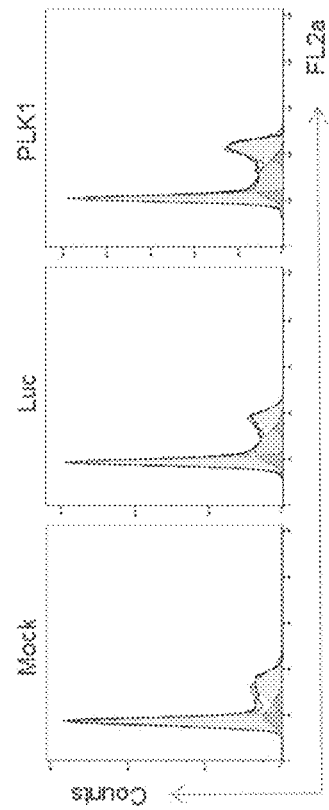
FIGS. 7A-C. TsiLNP-mediated therapeutic gene silencing in a Mantle cell lymphoma (MCL) (A) PLK1 gene knockdown, relative to GAPDH, by qRT-PCR in Granta-519 cells incubated with PLK1 or luciferase siRNA-loaded TsiLNP. Data are mean±SD, n=3, *p=0.0001 (two-sided Student's t-test.). (B) Representative cell cycle distribution, 60 h post treatments with αCD29-LNPs-siLuc or αCD29-LNPs-siPLK1, analyzed by flow cytometry. The data is representative of 3 independent experiments. (C) Survival curves of MCL-bearing mice. Corresponding treatments (2 mg siRNA/kg body) were administrated at seven time points as listed in the experimental section via retro-orbital route. n=10 animals per group, *P=0.003. P values and significance were determined by log-rank Mantel-Cox test with Bonferroni correction.
Figure 7B:
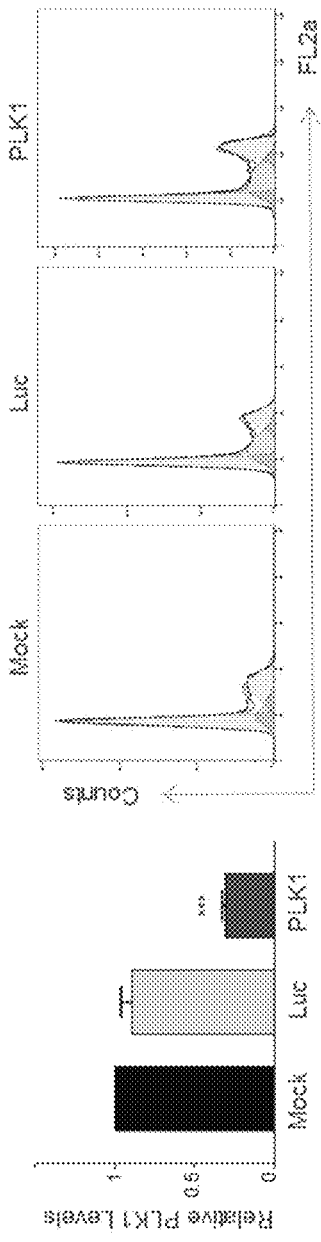
Figure 7C:
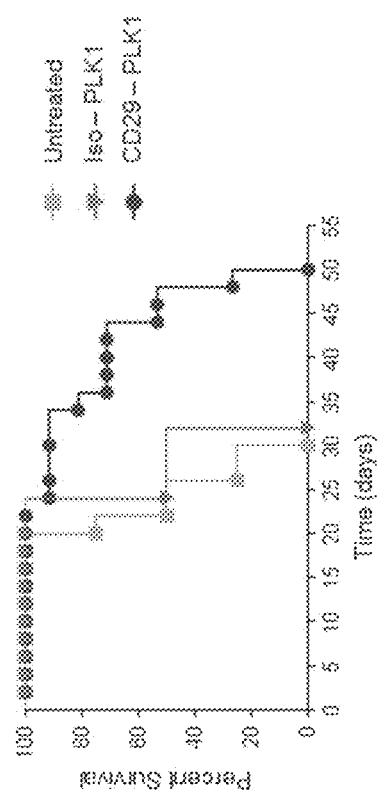

Whilst reducing the present invention to practice, the present inventors show that simply switching 8 different targeting antibodies (against CD44, CD34, Ly6C, CD3, CD4, CD25, CD29 and Itgb7) redirects the LNP for exquisitely specific uptake in diverse leukocyte subsets that express these cell-surface antigens in vivo and specific knockdown even in difficult-to-transfect CD4+ cells (FIG. 3D). Intravenously injected anti-Ly6C-coated LNP encapsulating TNF siRNAs were taken up selectively by Ly6C+ monocytes and activated tissue macrophages, suppressed TNF-α expression in the colon and ameliorated inflammatory bowel disease symptoms in a DSS-induced colitis mouse model (FIGS. 4A-H). Anti-CD29-coated LNPs entrapping Polo-like kinase 1 (PLK1) siRNAs prolonged survival of mice bearing Mantle Cell Lymphoma xenografts (FIGS. 7A-C). These data demonstrate the platform's potential utility for studying gene function in vivo and for targeted therapeutic applications. Adapting this flexible platform for human use will enable personal therapy for cancer patients in which the targeted antibody can be adjusted according to each patient's cancer cell surface marker expression. The platform could also allow the use of more than one targeting antibody to reduce the chance of cancer resistance due to receptor down-modulation.

Thus, according to a first aspect of the present invention there is provided a lipidated secondary antibody.

The term "antibody" as used in this invention includes intact molecules as well as functional fragments thereof.

As used herein the phrase "secondary antibody" refers to an antibody which binds to conserved regions of a primary antibody. Thus, the secondary antibody has a specificity for the antibody species and optionally isotype of the primary antibody.

Varieties of secondary antibody are available for particular antibody classes and fragment types. Secondary antibodies can bind parts of whole IgG (heavy and light chains, H+L), or only the Fab or Fc region, or only the gamma chain. Secondary antibodies also exist that are specific for IgM heavy chains (μ or Fc5μ), or the λ or κ light chains common to all immunoglobulins (IgG, IgA, IgD, IgE and IgM).

According to a particular embodiment, the secondary antibody is a monoclonal antibody (as further described herein below), for example a humanized monoclonal antibody.

The secondary antibody can belong to any antibody class (e.g., IgG, IgA, IgD, IgE and IgM) or isotype. According to a specific embodiment, the secondary antibody is selected from the group consisting of IgG1, IgG2, IgG3 and IgG4.

The secondary antibodies may be provided as intact antibodies (e.g., whole IgG) or as divalent F(ab')$_2$ fragments and monovalent Fab fragments, though other forms of antibody fragments, as described herein below can be used.

As used herein, the phrase "antibody fragment" refers to a functional fragment of an antibody (such as Fab, F(ab')$_2$, Fv, scFv, dsFv, or single domain molecules such as VH and VL) that is capable of binding to an epitope of an antigen.

According to a particular the antibody or antibody fragment comprises a constant region.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as a Fv, a single chain Fv (scFv), a disulfide-stabilized Fv (dsFv), an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab') 2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies are composed of a single VH or VL domains which exhibit sufficient affinity to the antigen.

In one embodiment, the fragment is a scFv.

In one embodiment, the secondary antibody may be an antibody fragment that binds to the Fc constant region of Rat IgG2a antibodies. In another embodiment, the secondary antibody may be an antibody fragment that binds to the Fc constant region of human antibodies (for example IgG antibodies). The secondary antibody (or fragment thereof, such as the scFv) should have sufficient affinity to avoid exchange with serum IgG e.g. having a Kd between $10^{-10}$M to $10^{-8}$M.

As mentioned, the secondary antibody of this aspect of the present invention is lipidated.

According to a particular embodiment, the polypeptide sequence of the secondary antibody contains an N-terminal sequence which is derived from a leader peptide recognized by a bacterial lipidation system. After removal of the leader peptide during export through the inner membrane, the mature polypeptide contains the N-terminal sequence of the leader peptide (e.g. CDQSSS—SEQ ID NO: 13) which is targeted by the lipidation system, resulting in lipid-acylation of the cysteine). It will be appreciated that in this embodiment, there is no linker sequence between the antibody itself and the lipidated portion of the antibody—rather the antibody itself is directly lipidated.

In one embodiment, the signal sequence is part of an inner membrane bacterial (e.g. *E. coli*) lipoprotein.

One example of an inner membrane lipoprotein is NlpA. (new lipoprotein A). The first six amino acid of NipA can be used as an N terminal anchor (CDQSSS: SEQ ID NO: 1013). Other examples of anchors that may find use with the invention include lipoproteins, Pullulanase of *K. pneumoniae*, which has the CDNSSS (SEQ ID NO: 17) mature lipoprotein. anchor, phage encoded celB, and *E. coli* acrE (envC).

Examples of inner membrane proteins which can be used as protein anchors include: AraH, MglC, MalF, MalG, Mal C, MalD, RbsC, RbsC, ArtM, ArtQ, GlnP, ProW, HisM, HisQ, LivM, LivA, Liv E, Dpp B, DppC, OppB, AmiC, AmiD, BtuC, FhuB, FecC, FecD, FecR, FepD, NikB, NikC, CysT, CysW, UgpA, UgpE, PstA, PstC, PotB, PotC, PotH, PotI, ModB, NosY, SecY, TolC, Dsb, B, DsbD, TonB, TatC, CheY, TraB, Exb D, ExbB and Aas. Further, a single transmembrane loop of any cytoplasmic protein can be used as a membrane anchor.

In another embodiment, the secondary antibody is attached to a lipidated peptide.

The lipidated peptide of this aspect of the present invention may be attached to the C or N terminus of the secondary antibody. In one embodiment, it is attached to the N terminus of the secondary antibody. The lipidated peptide may be attached directly to the secondary antibody or by way of a linker peptide.

The lipidated antibody of this aspect of the present invention may further comprise additional elements to aid in purification and/or identification. Table 1A provides non-limiting examples of identifiable moieties and purification moieties which can be conjugated to the secondary antibody of the invention.

TABLE 1A

| Moiety | Amino Acid sequence: | Nucleic Acid sequence: |
|---|---|---|
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR- SEQ ID NO: 18 | |
| orange fluorescent protein | AAL33917 | AF435432 |
| Beta galactosidase | ACH42114 | EU626139 |
| Streptavidin | AAM49066 | AF283893 |

In order to express the fusion protein of this aspect of the present invention, a polynucleotide sequence encoding the elements described above is preferably ligated into a nucleic acid construct suitable for host cell expression. Such a nucleic acid construct includes a promoter sequence for directing transcription of the polynucleotide sequence in the cell in a constitutive or inducible manner.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the fusion protein from a host cell in which it is placed.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Exemplary promoters contemplated by the present invention include, but are not limited to polyoma, Simian Virus 40 (SV40), adenovirus, retroviruses, hepatitis-B virus and cytomegalovirus promoters. According to a particular embodiment, the promoter is a bacterial promoter.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl.

Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide. \

It will be appreciated that the individual elements comprised in the expression vector can be arranged in a variety of configurations. For example, enhancer elements, promoters and the like, and even the polynucleotide sequence(s) encoding the fusion protein can be arranged in a "head-to-tail" configuration, may be present as an inverted complement, or in a complementary configuration, as an antiparallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein.

Recombinant viral vectors are useful for in vivo expression of the fusion protein since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al., [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the secondary antibody attached to the lipidated peptide and a heterologous protein can be engineered. Such a fusion protein can be designed so that the fusion protein can be readily isolated by affinity chromatography; e.g., by immobilization on a column specific for the heterologous protein. Where a cleavage site is engineered between the "fusion" protein and the heterologous protein, the "fusion" protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

Additional bacterial systems contemplated by the present invention include but are not limited to *Lactoccocus lactis, Pseudomonas, Streptomyces*, coryneform bacteria, and halophilic bacteria.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

Since the secondary antibody is lipidated, it is inserted into the membranes of the expressing cells. The membrane fraction may be isolated (e.g. by centrifugation) and the lipidated secondary antibody may be extracted from the membranes using detergent before optionally being further purified (e.g. using Nickel affinity chromatography).

Following isolation, the lipidated secondary antibody described herein may be contacted with a particle to generate an immunoparticle. It will be appreciated that lipidated proteins (other than the above described lipidated secondary antibodies) that are capable of immunocomplexing with the Fc portion of a primary antibody are also contemplated for generating the immunoparticles. Such proteins include Protein A, Protein G, Protein L, Protein Z, Protein LG, Protein LA and Protein AG. Examples of additional proteins that may be lipidated and used to generate the immunoparticles of the present invention are described in Lombardi et al., Discovery Today, Volume 20, Number 10, Pages 1271-1283, October 201; Braisted et al., Proc. Natl. Acad. Sci. USA, Vol. 93, pp. 5688-5692, June 1996; and Y. J. Jeong et al., Peptides 31 (2010) 202-206, the contents of which are incorporated herein by reference.

The contacting is effected for a length of time (e.g. 6-72 hours) and under conditions (e.g. temperature) that allow the lipidated portion of the protein (e.g. secondary antibody) to insert into the immunoparticle. It will be appreciate that the lipidated protein (e.g. secondary antibody) is thus non-covalently attached to the particle via its lipidated portion.

The lipidated protein (e.g. secondary antibody) of the invention couples on the outer surface of the particle. Measures are taken to couple the protein (e.g. antibody) without significantly affecting its functionality in binding the primary antibody (i.e., more than 80%, 90% or 95% of the secondary antibodies on the particle are available for binding the primary antibody) and the particle's loadability or loading with the pharmaceutical agent.

Thus, the lipidated protein (e.g. secondary antibody) is coupled to the outer surface of the particle and not via the primary antibody. In such an orientation the lipidated protein (e.g. secondary antibody) is a linker for the primary antibody i.e., the lipidated protein (e.g. secondary antibody) links the primary antibody to the particle. According to a specific embodiment, the binding of the secondary antibody is not via the CDRs of the secondary antibody e.g., via the conserved regions e.g., the Fc region. Alternatively, via the N terminal or the C-terminal of the secondary antibody e.g., in the case of a scFv. The binding of the secondary antibody to the particles surface may be via a linker as further described herein.

As used herein the term "immunoparticle" refers to a particle which typically serves as a drug carrier to which an antibody has been coupled on a surface thereof.

As used herein, "particles" refers to nano to micro structures which are not biological cells.

The particle may be a synthetic carrier, gel or other object or material having an external surface which is capable of being loadable with (e.g., encapsulating) a pharmaceutical agent. The particle may be either polymeric or non-polymeric preparations.

Exemplary particles that may be used according to this aspect of the present invention include, but are not limited to polymeric particles, microcapsules, liposomes, microspheres, microemulsions, nanoparticles, nanocapsules, nano-spheres, nano-liposomes, nano-emulsions and nano-tubes.

In one embodiment, the particle is a biological particle—e.g. an erythrocyte or a cell ghost.

In another embodiment, the particle is a non-biological particle—i.e. not a cell.

According to a particular embodiment, the particles are nanoparticles.

As used herein, the term "nanoparticle" refers to a particle or particles having an intermediate size between individual atoms and macroscopic bulk solids. Generally, nanoparticle has a characteristic size (e.g., diameter for generally spherical nanoparticles, or length for generally elongated nanoparticles) in the sub-micrometer range, e.g., from about 1 nm to about 500 nm, or from about 1 nm to about 200 nm, or of the order of 10 nm, e.g., from about 1 nm to about 100 nm. The nanoparticles may be of any shape, including, without limitation, elongated particle shapes, such as nanowires, or irregular shapes, in addition to more regular shapes, such as generally spherical, hexagonal and cubic nanoparticles. According to one embodiment, the nanoparticles are generally spherical.

The particles of this aspect of the present invention may have a charged surface (i.e., positively charged or negatively charged) or a neutral surface.

Agents which are used to fabricate the particles may be selected according to the desired charge required on the outer surface of the particles.

Thus, for example if a negatively charged surface is desired, the particles may be fabricated from negatively charged lipids (i.e. anionic phospholipids) such as described herein below.

When a positively charged surface is desired, the particles may be fabricated from positively charged lipids (i.e. cationic phospholipids), such as described herein below.

As mentioned, non charged particles are also contemplated by the present invention. Such particles may be fabricated from neutral lipids such as phosphatidylethanolamine or dioleilphosphatidylethanolamine (DOPE).

It will be appreciated that combinations of different lipids may be used to fabricate the particles of the present invention, including a mixture of more than one cationic lipid, a mixture of more than one anionic lipid, a mixture of more than one neutral lipid, a mixture of at least one cationic lipid and at least one anionic lipid, a mixture of at least one cationic lipid and at least one neutral lipid, a mixture of at least one anionic lipid and at least one neutral lipid and additional combinations of the above. In addition, polymer-lipid based formulations may be used.

There are numerous polymers which may be attached to lipids. Polymers typically used as lipid modifiers include, without being limited thereto: polyethylene glycol (PEG), polysialic acid, polylactic (also termed polylactide), polyglycolic acid (also termed polyglycolide), apolylactie-polyglycolic acid' polyvinyl alcohol, polyvinylpyrrolidone, polymethoxazoline, polyethyloxazoline, polyllydroxyetly-loxazolille, solyhydroxypryloxazoline, polyaspartarllide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose.

The polymers may be employed as homopolymers or as block or random copolymers.

The particles may also include other components. Examples of such other components includes, without being limited thereto, fatty alcohols, fatty acids, and/or cholesterol esters or any other pharmaceutically acceptable excipients which may affect the surface charge, the membrane fluidity and assist in the incorporation of the biologically active lipid into the lipid assembly. Examples of sterols include cholesterol, cholesterol hemisuccinate, cholesterol sulfate, or any other derivatives of cholesterol. Preferred lipid assemblies according the invention include either those which form a micelle (typically when the assembly is absent from a lipid matrix) or those which form a liposome (typically, when a lipid matrix is present).

In one embodiment, the particle is a lipid-based nanoparticle. The core of the particle may be hydrophilic or hydrophobic. The core of the lipid-based nanoparticle may comprise some lipids, such that it is not fully hydrophilic.

In a specific embodiment, the particle is a liposome. As used herein and as recognized in the art, liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3): 35-43].

The liposomes may be unilamellar or may be multilamellar. Unilamellar liposomes may be preferred in some instances as they represent a larger surface area per lipid mass. Suitable liposomes in accordance with the invention are preferably non-toxic. The liposomes may be fabricated from a single phospholipid or mixtures of phospholipids.

The liposomes may also comprise other lipid materials such as cholesterol. For fabricating liposomes with a negative electrical surface potential, acidic phospho- or sphingo- or other synthetic-lipids may be used. Preferably, the lipids have a high partition coefficient into lipid bilayers and a low desorption rate from the lipid assembly. Exemplary phospholipids that may be used for fabricating liposomes with a negative electrical surface potential include, but are not limited to phosphatidylserine, phosphatidic acid, phosphatidylcholine and phosphatidyl glycerol.

Other negatively charged lipids which are not liposome forming lipids that may be used are sphingolipids such as cerebroside sulfate, and various gangliosides.

The most commonly used and commercially available lipids derivatized into lipopolymers are those based on phosphatidyl ethanolamine (PE), usually distearylphosphatidylethanolamine (DSPE).

The lipid phase of the liposome may comprise a physiologically acceptable liposome forming lipid or a combination of physiologically acceptable liposome forming lipids for medical or veterinarian applications. Liposome-forming lipids are typically those having a glycerol backbone wherein at least one of the hydrofoil groups is substituted with an acyl chain, a phosphate group, a combination or derivatives of same and may contain a chemically reactive group (such as an as amine imine, acids ester, aldelhyde or alcohol) at the headgroup. Typically, the acyl chain is between 12 to about 24 carbon atoms in length, and has varying degrees of saturation being fully, partially or non-hydrogenated lipids. Further, the lipid matrix may be of natural source, semi-synthetic or fully synthetic lipid, and neutral, negatively or positively charged.

According to one embodiment, the lipid phase comprises phospholipids.

The phospholipids may be a glycerophospholipid. Examples of glycerophospholipid include, without being limited thereto, phosphatidylglycerol (PG) including dimyristoyl phosphatidylglycerol (DMPG); phosphatidylcholine (PC), including egg yolk phosphatidylcholine and dimyristoyl phosphatidylcholine (DMPC), phosphatidic acid (PA), phosphatidylinositol (PI), phosphatidylserine (PS) and sphingomyelin (SM) and derivatives of the same.

Another group of lipid matrix employed according to the invention includes cationic lipids (monocationic or polycationic lipids). Cationic lipids typically consist of a lipophilic moiety, such as a sterol or the same glycerol backbone to which two acyl or two alkyl, or one acyl and one alkyl chain contribute the hydrophobic region of the amphipathic molecule, to form a lipid having an overall net positive charge.

Preferably, the head groups of the lipid carry the positive charge. Monocationic lipids may include, for example, 1,2-dimyristoyl-3-trimethylammonium propane (DMTAP) 1,2-dioleyloxy-3-(trimethylanino) propane (DOTAP), N-[-1-(2,3-ditetradecyloxy)propyl]-N,N-dimethyl-N-hydroxyethylammonium bromide (DMRIE), N-[1-(2,3-dioleyloxy)propyl]-N,N-dimethyl-N-hydroxy ethyl-ammonium bromide (DORIE), N-[1-(2,3-dioleyloxy) propyl];-N,N,N-trimethylammonium chloride (DOTMA); 3; N—(N',N'-dimethylaminoethane) carbamoly]; cholesterol (DC-Chol), and 1 dimethyl-dioctadecylammonium (DDAB).

Examples of polycationic lipids include a similar lipoplilic moiety as with the mono cationic lipids, to which spermine or spermidine is attached. These include' without being limited thereto, N-[2-[[2,5-bis[3-aminopropyl) amino]-1-oxopentyl]amino]ethyl]N,N dimethul-2,3 bis (1-oXo-9-octadecenyl) oXy];-1 propanaminium (DOSPA), and ceramide carbamoyl spermine (CCS).

The cationic lipids may be used alone, in combination with cholesterol, with neutral phospholipids or other known lipid assembly components. In addition, the cationic lipids may form part of a derivatized phospholipids such as the neutral lipid dioleoylphosphatidyl ethanolamine (DOPE) derivatized with polylysine to form a cationic lipopolymer.

The diameter of the liposomes used preferably ranges from 50-200 nM and more preferably from 20-100 nM. For sizing liposomes, extrusion, homogenization or exposure to ultrasound irradiation may be used, Homogenizers which may be conveniently used include microfluidizers (produced by Microfluidics of Boston, Mass., USA) or microfluidic micro mixer (Precision NanoSystems, Vancouver, BC, Canada). In a typical homogenization procedure, liposomes are recirculated through a standard emulsion homogenizer until selected liposomes sizes are observed. The particle size distribution can be monitored by conventional laser beam particle size discrimination. Extrusion of liposomes through a small-pore polycarbonate membrane or an asymmetric ceramic membrane is an effective method for reducing liposome sizes to a relatively well defined size distribution. Typically, the suspension is cycled through the membrane one or more times until the desired liposome size distribution is achieved. The liposomes may be extruded through successively smaller pore membranes to achieve a gradual reduction in liposome size.

According to another embodiment, the particle is a nanoparticle. Preferably, nanoparticles are less than 100 nm in diameter and can be spherical, non-spherical, or polymeric particles. In a preferred embodiment, the polymer used for fabricating nanoparticles is biocompatible and biodegradable, such as poly(DL-lactide-co-glycolide) polymer (PLGA). However, additional polymers which may be used for fabricating the nanoparticles include, but are not limited to, PLA (polylactic acid), and their copolymers, polyanhydrides, polyalkyl-cyanoacrylates (such as polyisobutylcyanoacrylate), polyethyleneglycols, polyethyleneoxides and their derivatives, chitosan, albumin, gelatin and the like.

The particles of the present invention may be modified. According modified to enhance their circulatory half-life (e.g. by PEGylation) to reduce their clearance, to prolong their scavenging time-frame and to allow antibody binding. The PEG which is incorporated into the particles may be characterized by of any of various combinations of chemical composition and/or molecular weight, depending on the application and purpose.

It will be appreciated that once an immunoparticle is generated, it may be packed in a container and identified as a universal kit for in-vivo delivery of a pharmaceutical agent. The kit may further comprise instructions for performing immunocomplexation of the immunoparticles with the primary antibody.

Drugs or therapeutic agents that may be loaded into the particles include but are not limited to anticancer agent (e.g., chemotherapy, radioisotopes, immunotherapy), antibiotic, enzyme, antioxidant, lipid intake inhibitor, hormone, anti-inflammatory, steroid, vasodilator, angiotensin converting enzyme inhibitor, angiotensin receptor antagonist, inhibitor for smooth muscle cell growth and migration, platelet aggregation inhibitor, anticoagulant, inhibitor for release of chemical mediator, promoter or inhibitor for endothelial cell growth, aldose reductase inhibitor, inhibitor for mesangium cell growth, lipoxygenase inhibitor, immunosuppressive, immunostimulant, antiviral agent, Maillard reaction suppressor, amyloidosis inhibitor, nitric oxide synthetic inhibitor, AGEs (Advanced glycation endproducts) inhibitor, radical scavenger, protein, peptide; glycosaminoglycan and derivatives thereof; and oligosaccharide, polysaccharide, and derivatives thereof.

In another embodiment, the particles are loaded with a diagnostic agent.

Exemplary diagnostic drugs include in vivo diagnostics such as an X ray contrast medium, a diagnostic agent for ultrasound, an isotope-labeled agent for diagnosis by nuclear medicine, and an agent for diagnosis by nuclear magnetic resonance.

Loading of the particle with the pharmaceutical agent can be effected concomitant with, or following particle assembly.

Thus, in one preferred embodiment, for example, when the pharmaceutical agent is a nucleic acid, e.g., DNA, RNA, siRNA, plasmid DNA, short-hairpin RNA, small temporal RNA (stRNA), microRNA (miRNA), RNA mimetics, or heterochromatic siRNA, the nucleic acid agent of interest has a charged backbone that prevents efficient encapsulation in the lipid particle. Accordingly, the nucleic acid agent of interest may be condensed with a cationic polymer, e.g., PEI, polyamine spermidine, and spermine, or cationic peptide, e.g., protamine and polylysine, prior to encapsulation in the lipid particle. In one embodiment, the agent is not condensed with a cationic polymer.

In another embodiment, the agent of interest is encapsulated in the lipid particle in the following manner. The immunoparticle is provided lyophilized. The agent of interest is in an aqueous solution. The agent of interest in aqueous solution is utilized to rehydrate the lyophilized lipid particle. Thus, the agent of interest is encapsulated in the rehydrated lipid particle.

In one embodiment, more than one agent of interest may be delivered by the immunoparticles (e.g., lipid-based particle) of this aspect of the present invention. For example, two or more agents may be delivered, where both (or all) the agents are hydrophilic. In another example, two or more agents may be delivered, where both (or all) the agents are hydrophobic.

In one embodiment, two cargo agents of interest may be delivered by the immunoparticles (e.g., lipid-based particle). One cargo agent may be hydrophobic and the other hydrophilic. The hydrophobic agent may be added to the lipid particle during formation of the lipid particle. The hydrophobic agent associates with the lipid portion of the lipid particle. The hydrophilic agent is added in the aqueous solution rehydrating the lyophilized lipid particle. In an exemplary embodiment of two agent delivery, a condensed siRNA is encapsulated in a liposome and a drug that is poorly soluble in aqueous solution is associated with the lipid portion of the lipid particle. As used herein, "poorly soluble in aqueous solution" refers to a composition that is less that 10% soluble in water.

Any suitable lipid: pharmaceutical agent ratio that is efficacious is contemplated by this invention. Preferred lipid: pharmaceutical agent molar ratios include about 2:1 to about 30:1, about 5:1 to about 100:1, about 10:1 to about 40:1, about 15:1 to about 25:1.

According to a specific embodiment, the fusion protein: siRNA weight ratio is about 1:20, 1:30, 1:36 or even 1:50.

The preferred loading efficiency of pharmaceutical agent is a percent encapsulated pharmaceutical agent of about 50%, about 60%, about 70% or greater. In one embodiment, the loading efficiency for a hydrophilic agent is a range from 50-100%. The preferred loading efficiency of pharmaceutical agent associated with the lipid portion of the lipid particle, e.g., a pharmaceutical agent poorly soluble in aqueous solution, is a percent loaded pharmaceutical agent of about 50%, about 60%, about 70%, about 80%, about 90%, about 100%. In one embodiment, the loading efficiency for a hydrophobic agent in the lipid layer is a range from 80-100%.

As used herein "loading" refers to encapsulating or absorbing.

The term "encapsulated" as used herein refers to the pharmaceutical agent being distributed in the interior portion of the particles. Preferably, the pharmaceutical agents are homogenously distributed. Homogeneous distribution of a pharmaceutical agent in polymer particles is known as a matrix encapsulation. However, due to the manufacturing process it is foreseen that minor amounts of the pharmaceutical agent may also be present on the outside of the particle and/or mixed with the polymer making up the shell of the particle.

As used herein "absorbed" refers to binding of the pharmaceutical agent to the outer surface of the particle.

The desired amount of the drug loaded in the particle varies depending on the type of the drug. However, it is preferable that the drug can be loaded in the particle at a high loading efficiency.

Once the lipidated polypeptide (e.g. secondary antibody) is conjugated to the particle via the lipidated peptide motif, the present invention contemplates contacting the immunoparticle with a primary antibody.

As used herein the term "primary antibody" refers to an antibody (or antibody fragment as defined herein) which specifically recognizes an antigenic target of interest (e.g., a protein, peptide, carbohydrate, or other small molecule) and is typically unconjugated (unlabelled). Primary antibodies that recognize and bind with high affinity and specificity to unique epitopes across a broad spectrum of biomolecules are available as high specificity (e.g., 1 µM to 0.5 nM) monoclonal antibodies and/or as polyclonal antibodies.

According to a specific embodiment, the primary and/or the secondary antibody is a monoclonal antibody.

According to a specific embodiment, the primary antibody comprises an antigen recognition domain which binds a tissue or tumor specific antigen.

As used herein "a tissue specific antigen" refers to a heterogenetic antigen with organ or tissue specificity.

As used herein "a tumor (or cancer) specific antigen" refers to an antigenic substance produced in tumor cells, i.e., it triggers an immune response in the host. Tumor antigens are useful in identifying tumor cells and are potential candidates for use in cancer therapy. The term also encompasses tumor associated antigens.

According to a specific embodiment, the antigen recognized by the primary antibody is a cell-surface antigen.

In particular, the antigen recognized by the primary antibodies is CD44, CD34, Ly6C, CD3, CD4, CD25, CD29 and/or Itgb7.

It will be appreciated that to improve specificity, the primary antibody refers to a plurality of primary antibodies that bind different targets e.g., 2, 3 or 4 distinct targets. Thus, one target may be a tissue specific antigen while the other(s) can be a tumor specific antigen or vise a versa. Alternatively, all the primary antibodies bind tissue (cell) specific antigens. Yet alternatively all the primary antibodies bind tumor specific antigens. According to a specific embodiment, the primary antibody is a monoclonal antibody.

According to a specific embodiment, the primary antibody is a bispecific antibody.

According to a specific embodiment, the primary antibody is conjugated to a pharmaceutical agent.

According to a specific embodiment, immunocomplexation of the primary antibody with the secondary antibody, refers to antibody (i.e., secondary antibody)-antigen (i.e., primary antibody)-based interaction. Antibody-antigen binding is a non-covalent, reversible interaction (specific binding is typically in the 1 µM-0.1 nM range), which fully maintains the functionality of the primary antibody in binding its epitope. According to a specific embodiment, the immunocomplexation reaction is effected ex-vivo.

It will be appreciated that the present inventors also contemplate immunocomplexation of particular polypeptides (described herein above) to the FC portion of the primary antibody. In this case, the immunocomplexation is also typically a non-covalent reversible interaction, which fully maintains the functionality of the primary antibody in binding its epitope.

The weight ratio of secondary antibody:primary antibody is typically 1:1, although other ratios such as 1:2, 2:1, 1:3, 3:1 are also contemplated.

Conditions for performing immunocomplexation are well known in the art and require physiological conditions and avoid high salt concentrations and extremes of pH which disrupt antigen-antibody binding by weakening electrostatic interactions and/or hydrogen bonds.

Methods of producing polyclonal and monoclonal antibodies (either the primary or the secondary antibodies described herein) as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Since the immunoparticles of the present invention are typically used in pharmaceutical applications, they are generated non-immunogenic in the subject administered therewith.

Thus, according to a specific embodiment, the secondary antibody and optionally the primary antibody are humanized. Methods of humanizing antibodies are provided hereinabove. According to a further specific embodiment, the humanized monoclonal secondary antibody is isolated. As used herein the term "isolated" refers to retrieved from the human body and optionally further purified. Isolated can be a purified preparation which includes at least 90% antibody of interest (e.g., primary or secondary) and less than 10% other immunoglobulins.

According to a specific embodiment, the primary antibody is a humanized antibody. In one example the primary and the secondary antibody are purified recombinant monoclonal antibodies (or mixtures thereof) The particles of the present invention may be administered to the subject per se or as part of a pharmaceutical composition in order to treat a disease. As used herein a "pharmaceutical composition" refers to a preparation of the particles encapsulating the active ingredients described herein with other chemical components such as physiologically suitable carriers and excipients.

It will be appreciated that the particles can be used to treat any disease depending on the therapeutic agent that is loaded therein.

Thus, for example, if the immunoparticles are loaded with an siRNA to TNFalpha, they may be used to treat immune related diseases such as colitis and IBD. According to a particular embodiment, the primary antibody which is used for this application is Ly6C.

Other gene targets for IBD include but are not limited to Cyclin D1, IL-6, IL-2, RORgt. Additional primary antibodies for IBD include but are not limited to Itbg7, CCR9 and CCR7.

Furthermore, if the immunoparticles are loaded with an siRNA to PLK1, they may be used to treat cancer, such as lymphoma. Other gene targets for cancer may include but are not limited to eIF3c, PD-L1 and VEGF.

According to a particular embodiment, the primary antibody which is used for this application is CD29, Her2, EGFR (for targeting cancer cells). It will be appreciated that the platform can be used to target not only cancer cells, but also to manipulate other cell populations that support cancer progression such as macrophages and Tregs using Ly6C or GARP, respectively.

Depending on the pharmaceutical agent loaded in the immunoparticles and the primary antibody decorated thereupon, additional cancers which may be treated using the particles of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Inflammatory conditions that may be treated using the immunoparticles of this aspect of the present invention are summarized infra.

Inflammatory diseases—include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (*Datta* SK., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2): 157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, *mycoplasma* diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment, the pharmaceutical composition comprises an immunoparticle comprising a monoclonal secondary antibody (e.g., humanized) immunocomplexed with a primary antibody, wherein the monoclonal secondary antibody is coupled on an outer surface of a particle via a lipidated peptide and wherein the particle is loaded with a pharmaceutical agent.

According to a specific embodiment, the pharmaceutical agent is a therapeutic agent, as further described herein above.

The purpose of the pharmaceutical composition is to facilitate administration of the active ingredients to the subject.

Herein the term "active ingredient" refers to the pharmaceutical agents.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays—e.g. lysosomal enzyme comprising particles may be tested for in-vitro activity in plasma or in other plasma mimicking environments. For example, a dose can be formulated in animal models to achieve a desired tissue concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or tissue levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The immunoparticles of the present invention may be used to deliver a pharmaceutical agent to a subject in need thereof. Both therapeutic and clinical applications are contemplated herein.

Subjects who may be treated according to the methods described herein are typically mammalian subjects, e.g. human.

The present teachings can be used in a variety of clinical applications which will benefit from the implementation of such a simple and cost-effective platform.

It is expected that during the life of a patent maturing from this application many relevant particles will be developed and the scope of the term immunoparticle is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Secondary scFv construction, expression and purification Total RNA was extracted from hybridoma cells (ATCC, TIB-173) by EZ-RNA (Biological Industries, Israel) reagent, and cDNA was synthesized (Quanta Biosciences). Heavy and light IgG chains were cloned essentially as described in (11). Secondary scFv was assembled with an insertion of a $(Gly_4Ser)_3$ linker and cloned into pET22b-pelB vector, downstream to a Hexa Hisidine tag.

For periplasmic expression, E. coli Rosetta B L21 (DE3) cells were transformed with secondary scFv expression vector. At OD600 nm=2.5, 1 mM IPTG was added for 3 hours at 30° C. shaking at 250 RPM. Periplasmic proteins were extracted according to a standard protocols (12) and secondary scFv was purified using HisTrap HP columns (GE Healthcare Life Science) according to the supplier's recommendations.

ASSET Construction, Expression and Purification

For ASSET engineering we added a NlpA signal peptide and lipidation sequence at the secondary scFv N terminus by a set of PCR reactions. At the secondary scFv C terminus we added the red fluorescent protein mCherry followed by a hexa histidine tag. The DNA Sequence was validated by Sanger sequencing. E. coli BL21-tuner (DE3) cells transformed with ASSET expression vector. At OD600 nm=1, 0.5 mM IPTG was added for induction O.N at 30° C. ASSET was purified from the membrane fraction and solubilized in 20 mM TRIS(HCL) (PH 8) buffer with 1% Triton™ X-100 (Sigma-Aldrich), followed by buffer exchange to 1.4% Octyl glucoside (Ornat, Israel) as described previously (7, 8). ASSET was purified using HisTrap HP columns (GE Healthcare Life Science). For micelle creation, 250 nM cholesterol (Avanti Polar Lipids, USA) was added and ASSET was stored at −80° C., for.

Biacore

Binding affinity of purified mutated (m)ASSET to RIg antibodies was determined by Surface Plasmon Resonance (SPR) with a Biacore T-200 instrument. mASSET dilutions (0 to 30 nM) in HEPES-buffered saline (HBS) were flowed over immobilized RIg on a CM5 sensor chip (about 1000 RU immobilized IgGs). EDC/NHS immobilization was at a flow rate of 20 µl/min. Dissociation and association constants ($K_{d/a}$) were analyzed using Biacore evaluation software 4.1.

ELISA

ELISA plated were coated O.N with 5 µg/ml RIg (BioXcell, clone FIB504) or BSA, for control. After blocking for 2 hours at 37° C. with 3% skim milk in PBS, secondary scFv or ASSET were added in serial dilutions for 1 hour at RT. For detection mouse anti-His (Roche) was used followed by anti-mouse HRP. To test ASSET LNPs functionality, the same protocol was followed with an additional stage of LNPs pre-incubation with 0.2% Triton™ X-100 (Sigma-Aldrich) for 20 min at 37° C.

To test TsiLNPs and ccTsiLNPs RIg functionality, wells were coated O.N with 5 µg/ml recombinant mouse CD34 (Sino Biolgical Inc, PA). After blocking for 2h at 37° C. with 3% skim milk, TsiLNPs or ccTsiLNPs, pre-incubated with 0.2% Triton™ X-100 (Sigma-Aldrich), were added in serial dilutions for 1hour at room temperature (RT). anti-Rat HRP was used for detection. TMB solution (Millipore, USA) was used as a substrate and stopped by 2 M H2504. Results were obtained by a plate reader (Biotek) at OD 450 nm.

siRNAs

Chemically modified siRNAs against CD45 and luciferase were synthesized at IDT (Coralville, Iowa) using standard phosphoramidite chemistry.

```
CD45 siRNA:
sense strand:
                                        (SEQ ID NO: 1)
mCmUrGrGmCmUrGrArAmUmUmUmCrArGrArGmCrAdTsdT anti-sense strand:
                                        (SEQ ID NO: 2)
rUrGrCrUrCrUrGrArArArUrUmCrArGrCmCrArGdTsdT Luc siRNA:
sense strand:
                                        (SEQ ID NO: 3)
mCmUmUAmCrGmCmUrGrArGmUrAmCmUmUmCrGAdTsdT anti-sense strand:
                                        (SEQ ID NO: 4)
rUrCrGrArArGmUrArCrUmCrArGrCrGmUrArAGdTsdT TNFa siRNA:
sense strand:
                                        (SEQ ID NO: 5)
mGmUrCmUrCmArGrCrCrUrCmUrUmCrUmCrAmUrUrCrCrUrGmCT anti-sense strand:
                                        (SEQ ID NO: 6)
rArGmCrArGrGrArAmUrGmArGmArArGrArGrGrCrUrGrAmGrAm
CmAmU PLK1 dsiRNA:
sense strand:
                                        (SEQ ID NO: 7)
mGmCrUmUrAmArUrGrArCrGmArGmUrUmCrUmUrUrArCrUrUmCT anti-sense strand:
                                        (SEQ ID NO: 8)
rArGmArArGrUrArAmArGmArAmCrUrCrGrUrCrArUrUrAmArGm
CmAmG
m: 2'-OMe-modified nucleotides.
r: RNA bases.
phosphorothioate linkages are represented by "s".
```

Preparation of Lipid-Based Nanoparticles (LNPs) Entrapping siRNAs

LNPs were prepared by using microfluidic micro mixture (Precision NanoSystems, Vancouver, BC) as previously disclosed (13). Cholesterol (Chol), DSPC, and DSPE PEG-Mal were purchased (Avanti Polar Lipids, USA). Dlin-MC3-DMA (MC3) was synthesized according to previously described method (13). Briefly, one volume of lipid mixtures (MC3, DSPC, Cholesterol, DMG-PEG, and DSPE-PEG at 50:10.5:38:1.4:0.1 mol ratio) in ethanol and three volumes of siRNA (1:16 w/w siRNA to lipid) containing acetate buffer solutions were mixed by using dual syringe pump (model S200, kD Scientific, Holliston, Mass.) to drive the solutions through the micro mixer at a combined flow rate of 2 mL/min (0.5 mL/min for ethanol and 1.5 mL/min for aqueous buffer). The resultant mixture was dialyzed against phosphate buffered saline (PBS) (pH 7.4) for 16 hours to remove ethanol. For Cy5-labeled particles, 10% Cy5-labeled nontargeted siRNA was used. For carboxyl LNPs harboring functional group for conjugation, DSPE-PEG carboxyl was added to the lipid mixture (MC3, DSPC, Cholesterol, DMG-PEG, and DSPE-PEG carboxyl at 50:10:38:1.5:0.5 mol ratio).

Size Distribution

The sizes of LNPs were measured by dynamic light scattering using Malvern nano-ZS Zetasizer (Malvern Instruments Ltd., Worcestershire, UK). Size measurements were performed in PBS buffer.

Transmission Electron Microscopy (TEM) Analysis

A drop of aqueous solution containing LNPs or ASSET LNPs was placed on the carbon-coated copper grid and dried. The morphology of LNPs was analyzed by a JEOL 1200 EX (Japan) transmission electron microscope.

ASSET LNPs Incorporation and TsiLNPs Assembly

For ASSET incorporation to LNPs, ASSET was a simply incubated with LNPs for 48 hours at 4° C. (1:36, ASSET:siRNA weight ratio). To test incorporation efficiency, TsiLNPs were purified from possible free ASSET using dialysis with 1megaDalton cutoff (Biolab LTD, Israel). ASSET incorporation was measured via mCherry fluorescence and by functional ELISA. To construct TsiLNPs, RIg was added to ASSET LNPs for 30 min incubation (1:1, RIg:ASSET weight ratio). Possible Free RIg was removed using dialysis with 1megaDalton cutoff. Complex components were verified using western blot analysis. Detection of ASSET was done by using anti-His tag antibody (Roche) followed by HRP-conjugated goat anti-mouse antibody. RIg was detected by HRP-conjugated goat anti-Rat antibody. After optimizing RIg:ASSET ratio, no purification stages were required as all the RIg was incorporated.

siRNA Entrapment Efficiency siRNA encapsulation efficiency was determined by agarose gel electrophoresis as previously described (13). Briefly, the encapsulation efficiency was determined by comparing siRNA staining by Ethidium bromide between LNPs and ASSET LNPs in the presence and absence of 0.2% Triton™ X-100 (Sigma-Aldrich).

LNPs Quantification

To quantify LNPs after conjugation procedure or ASSET assembly procedure, Quant-iT™ RiboGreen™ RNA assay (Life Technology, CA, USA) was used as previously described (13). 2 µL of LNPs or dilutions of siRNA at known concentrations were diluted into a final volume of 100 µL of TE buffer (10 mM Tris-HCl, 20 mM EDTA) and 0.5% Triton™ X-100 (Sigma-Aldrich) in a 96-well fluorescent plate (Costar™ Corning™, NY, USA). The plate remained for 10 minutes at 40° C. to allow particles permeabilization. After incubation 99 µL of TE buffer and 1 µL of RiboGreen™ reagent were added to each well. Plates were shaken at room temperature for 5 minutes and reagent fluorescence (ex −485 nm, em −528 nm) was quantified using a plate reader (Biotek).

Confocal Microscopy Analysis 30 min after incubation of RAW 264.7 cells (ATCC, TIB-71) with TsiLNPS, self-assembled with anti-CD44 RIg (CEDARLANE, USA), or not, cell nuclei were stained with Hoechst 33342 (Sigma, Israel) and labeled with an anti-CD45 antibody. Cells were washed, and images were taken with a Nikon C2 (Nikon Instruments Inc., USA) confocal microscope.

Targeted LNPs Conjugation Procedure

To conjugate an anti-CD34 antibody (clone mec14.7, a generous gift from GARLANDA Cecilia, Humanitas Clinical and Research Center, Italy) to carboxyl functionalized LNPs, EDC, NHS, LNPs and anti-CD34 RIg were combined for 3 hours at RT followed by overnight (O.N) incubation at 4° C. To remove free anti-CD34, conjugated particles were loaded on Cl4b column. Particles fraction were combined and concentrated with Amicon cutoff 100 kD (Millipore).

Targeted LNPs Interaction with Fc Receptor 293 cells were co-transfected with a Fcgr2a (CD32) expression plasmid and GFP reporter using lipofectamine 2000 (Thermo Fisher Scientific) standard protocol. 48 hours after transfection, cells were harvest and subjected to 1 µg of siCy5 loaded LNPs, conjugated to anti-CD34 (ccTsiLNPs) or 1 µg of siCy5 entrapped with TsiLNPs, self-assembled with anti-CD34 RIg. As a control, cells were also subjected to lug siCy5 loaded naked LNPs (LNPs). Cy5 and GFP fluorescence was analyzed by flow cytometer (BD FACSCaliber). To score LNPs interaction with Fc receptor, Cy5 levels were calculated from GFP high cells, representing highly transfected cells and GFP negative cells, representing untransfected cells. The score for interaction was calculated as the ratio of geometric mean Cy5 fluorescence of GFP high and GFP low cell population.

Optimization of ASSET:RIg Ratio

ASSET LNPs encapsulating siCy5 were incubated for 10 min with increasing amounts of an anti-LFA1 antibody (clone M17/4) RIg (0-5:1, RIg:ASSET mole ratio). Total amount of 1 µg siCy5 loaded TsiLNPs were subjected to Tk1 cells for 15 min at 4° C. in DMEM (Biological Industries, Israel) supplemented with 10% serum. LNP binding was detected in flow cytometry.

TsiLNPs: In Vivo Silencing Using Anti CD4 RIg 10 week old C57BL6/J mice were obtained from the Animal Breeding Center, Tel Aviv University (Tel Aviv, Israel). All animal protocols were approved by the Tel Aviv Institutional Animal Care and Use Committee. Mice were maintained and treated according to the National Institutes of Health guidelines. TsiLNPs, self-assembled with anti-CD4 RIg containing siRNA against CD45 or luciferase were injected intravenously on day 1 and day 3 (3 mg/Kg). On day 5, inguinal lymph nodes were isolated and minced to make a single-cell suspension. Cells were washed twice with PBS followed by passing through a 70 µm cell strainer. Cells were then washed with PBS containing 1% fetal bovine serum and incubated with labeled anti-CD4, CD3 and CD45 antibodies (Biolegend, USA) for 30 min at 4° C. Cells were washed and analyzed on a Becton Dickinson FACScalibur flow cytometer with CellQuest software (Becton Dickinson, Franklin Lakes, N.J.). Data analysis was performed using FlowJo software (Tree Star, Inc., OR, USA).

TsiLNPs: In Vivo Binding Using Anti CD4 RIg 10 week old C57BL6/J mice were injected intravenously with siCy5 loaded TsiLNPs, self-assembled with different RIg: anti –Itgb 7 (BioXcell, USA), anti-CD3 (BioXcell, USA), anti-CD4 (BioXcell, USA) and anti-CD25 (R&D Systems, USA). 1.5 hours after injection, blood was collected in heparin-coated collection tubes, and the leukocytes were isolated by density centrifugation using ficoll paque plus (GE Healthcare). Cells were then washed with PBS containing 1% fetal bovine serum (Biological Industries, Israel) and incubated with labeled anti-CD4, CD8, CD3 and CD25 antibodies (Biolegend, USA) for 30 min at 4° C. and analyzed on a Becton Dickinson FACScalibur flow cytometer with CellQuest software (Becton Dickinson, Franklin Lakes, N.J.). Data analysis was performed using FlowJo software (Tree Star, Inc., OR, USA).

In-Vitro Silencing and qPCR

RAW 264.7 cells (ATCC, TIB-71) (60% confluence) in 24-well were treated with 0.5 µg of siTNFα or siLuc entrapped in LNPs. After 16 hours cells were washed and activated with 2.5 ng/ml IFNγ (Peprotech, USA). After 48 h, cells were harvested and mRNA was isolated using EZ-RNA (Biological Industries, Israel), and cDNA was prepared using a cDNA synthesis kit (Quanta Biosciences) mouse GAPDH was used as the endogenous control. Primer sequences: GAPDH FW: 5' TTG TGG AAG GGC TCA TGA CC 3' (SEQ ID NO: 9); GAPDH Rev: 5' TCT TCT GGG TGG CAG TGA TG 3' (SEQ ID NO: 10); TNFα FW: 5' GCA CCA CCA TCA AGG ACT CAA 3' (SEQ ID NO: 11); TNFα Rev: 5' TCG AGG CTC CAG TGA ATT CG 3' (SEQ ID NO: 12).

IBD Model

Colitis was induced in C57BL/6 mice with dextran sodium sulphate (DSS) as previously described (Ser. No. 18/239,128). Briefly, mice were fed for 8 days with 2% (wt/vol) DSS in the drinking water. Suspensions (200 µl) of TsiLNPs loaded with 1 mg/kg siRNAs against TNFα or Luciferase and self-assembled with anti-Ly6C or Isotype RIg (BioXcell, USA) were injected intravenously on days 3, 5 and 7. Body weight was monitored every other day. On day 8 mice colitis was assessed by colonoscopy and colitis severity was scored using colonoscopy scoring matrix (MEICS=Murine Endoscopic Index of Colitis). In addition, mice were sacrificed and the length of the entire colon was removed from cecum to anus and measured. Small segments of the colon were taken for histology histopathology and immunohistochemistry evaluations. In addition, cytokines were extracted from the colon using a homogenizer and measured using IL-6 and TNFα ELISA kits (R&D System, USA).

Mantle Cell Lymphoma Xenograft Model 8 week old female C.B-17/IcrHsd-Prkdc scid mice (n=10/ group) were treated, beginning 5 days after intravenous injection of 2.5×10[6] Granta 519 cells as described[5], with PBS (mock), isotype control RIg-LNP-siPLK1 or αCD29-LNP-siPLK1. LNPs containing 2 mg/kg siRNA were injected retro-orbitally on days 5, 8, 12, 15, 19, 22, and 26 after tumor injection. Response was assessed by survival. Mice that lost 15% body weight or developed limb paralysis were euthanized.

Statistical Analysis

Data were expressed mean±SD. Statistical analysis was performed using two-sided student's t test. Differences between or among groups are labeled as n.s. for not significant, * for $P \leq 0.05$,  for $P \leq 0.01$, * for $P \leq 0.001$ and **** for $P \leq 0.0001$.

Results

Figure 5A:
FIGS. 5A-B. Polyacrylamide/SDS gel electrophoresis of purified secondary scFv (A). Representative histograms demonstrating secondary scFv binding to TK1 cell line that was pre-incubated with Itgb7 RIg (red). Secondary scFv binding in the absence of RIg or in the absence of secondary scFv (gray) served as controls (B).
Figure 5B:
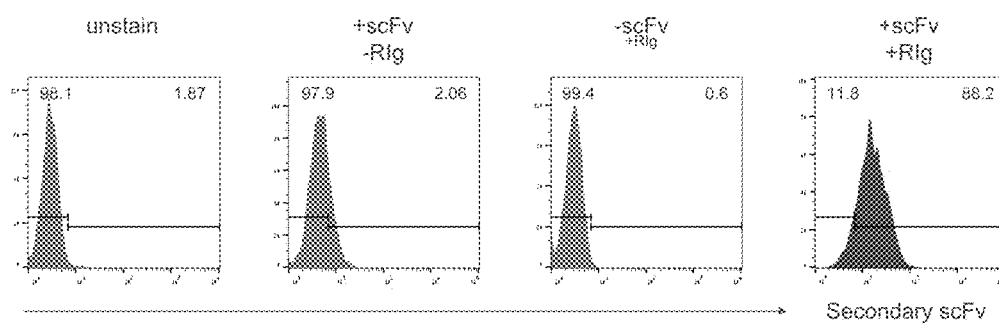

A recombinant lipoprotein (named ASSET, Anchored Secondary scFv Enabling Targeting) was designed for expression in *E. coli* that is composed of two functional domains—an N-terminal signal sequence and short CDQSSS (SEQ ID NO: 13) peptide NlpA motif that undergoes lipidation, fused to an scFv of a monoclonal antibody (clone RG7/1.30) (6) that binds to the Fc constant region of Rat IgG2a antibodies (RIg) (FIGS. 5A-B). The amino acid sequence of the VH domain of the antibody is set forth in SEQ ID NO: 14.

(EVQLLQSGPELVKPGASVKIPCKASGYTFTDYNMDWVKQSHEKSLEWIG

YINPYSGDTIYNHKFKDKATLTVYKSSNIAYMELRSLTSEDTAVYYCARG

GYDYGDHWGQGTTLTVSS).

The amino acid sequence of the VL domain (kappa) of the antibody is set forth in SEQ ID NO: 15

(DIKMTQSPSSMYASLGERVTITCKASQDINSYLSWFQQKPGKSPKTLIY

RANRLVDGVPSRFSGSGSGQDYSLTISSLEYEDMGIYYCLQDDEFPRTFG

GGTKLEIK).

The linker sequence of the antibody is set forth in SEQ ID NO: 16

(GSAGGGGSGGGGSGGGGS).

Figure 1A:
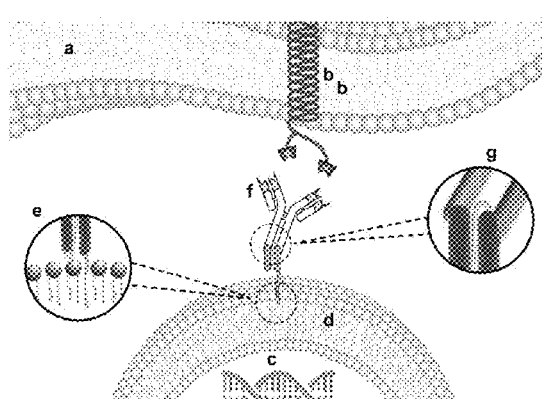
FIGS. 1A-J Schematic illustration of ASSET (Anchored Secondary scFv Enabling Targeting) design (A). target cell membrane (a); cell-surface target molecule (b); encapsulated siRNA (c); LNP (d); ASSET anchoring to LNPs (e); Rat IgG2a (RIg) (f); site of interaction between ASSET and RIg (g). Schematic illustration of the targeting platform versatility through binding of diverse RIg primary antibodies to target different cell subsets (B). Schematic illustration of targeted siRNA-loaded LNPs (TsiLNPs) construction (C) anchored ASSET expression in $E.$ $coli$ periplasm (a); ASSET purification in micelles (b); Post insertion of ASSET into siLNPs (c); RIg assembly (d). Schematic illustration of ASSET expression vector (D). Polyacrylamide/SDS gel electrophoresis of purified ASSET (E). ASSET affinity estimation to RIg by ELISA (F). Representative histograms demonstrating ASSET binding to TK1 cell line that were pre-incubated with LFA-1 RIg. ASSET binding in the absence of RIg (Black) served as control. Mock cells appear in grey (G). Incorporation of ASSET (+) or lipidation-defective mASSET into LNP quantified by mCherry fluorescence determined by the fluorescence remaining in TsiLNP after dialysis to remove unbound protein (H) or assessed by ELISA after dialysis to remove unbound protein (I). Mutated (m)ASSET (0, 3, 6, 12, 18, and 30 nM) binding to RIg assessed by Biacore using immobilized Rig (J).
Figure 1B:
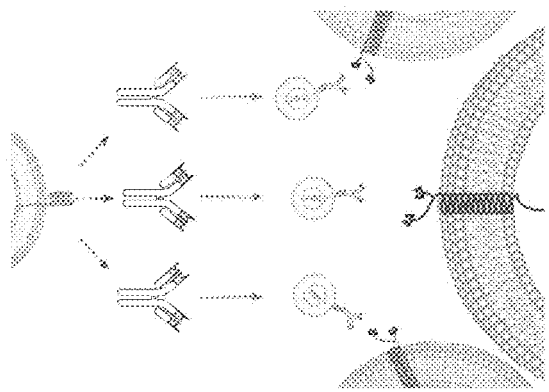
Figure 1C:
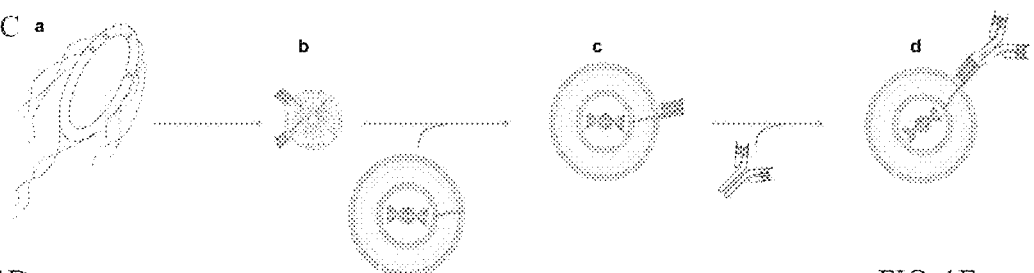
Figure 1D:

This lipidation strategy, previously used for displaying proteins anchored to the inner membrane of E. coli (7, 8), allows purified recombinant ASSET to be inserted into any lipid vesicle by post insertion (FIGS. 1A, C and D)(7, 8). An mCherry domain and His-tag were added to the C-terminus of the ASSET construct to enable the tracking and the uptake of ASSET-coated LNPs into cells and for the purification of the recombinant fusion protein, respectively.

Figure 1E:
Figure 1F:
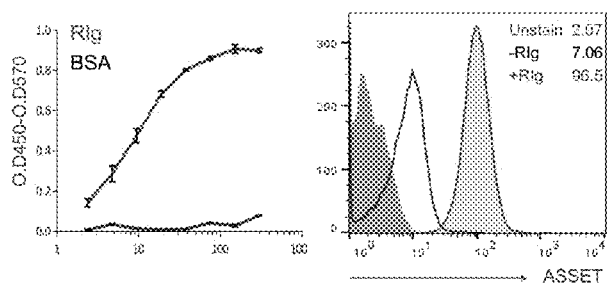
Figure 1G:
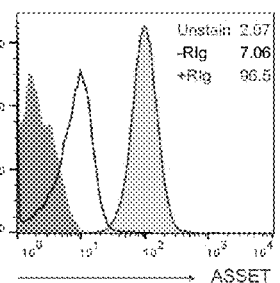
Figure 1H:
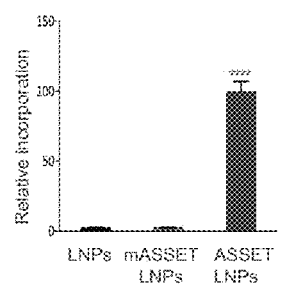
Figure 1I:
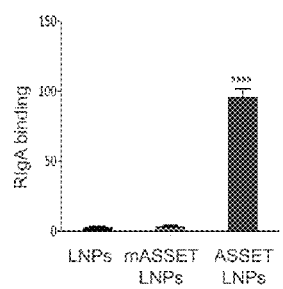
Figure 1J:
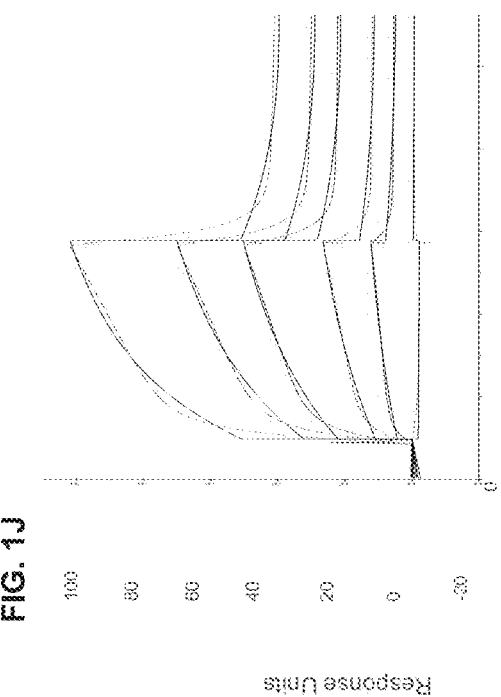

ASSET was expressed and purified from bacteria with high yield (30 mg/L), reasonable purity after a single step His-tag-based purification (~47.5%) (FIG. 1E) and with minimal endotoxin contamination (1.57 EU/Kg). Purified ASSET specifically bound RIg with a $K_d$ of ~10 nM (FIG. 1F) and pre-bound to cells (FIG. 1G). Purified mutated (m)ASSET, composed of a fusion protein containing a mutated NlpA motif, specifically bound to Rat IgG2a (RIg) with $K_d$ ~22.7 nM as measured by surface plasmon resonance (SPR) (FIG. 1J). When ASSET was incubated with LNPs containing siRNA, it was all incorporated (99.6% efficiency) as was quantified by ASSET mCherry (FIG. 1H). Incorporation required the NlpA lipidation motif since, a fusion protein containing a mutated NlpA motif (mASSET) failed to insert into lipid particles, suggesting that NlpA lipidation directed ASSET anchoring into LNPs. Notably, ASSET incorporation did not damage its affinity to RIg and maintained 95.8% of its functionality as was assessed by ELISA (FIG. 1I). ASSET incorporation slightly increased the size of the LNPs from 66±11 to 75±14 nm with a small increase in the polydispersity index (PDI) from 0.10 to 0.16 PDI by dynamic light scattering (Table 1B). These particles retained both their spherical shape (FIG. 6A) and efficient siRNA loading (FIG. 6B).

TABLE 1B

|  | LNPs | ASSET LNPs |
| --- | --- | --- |
| Hydrodynamic diameter (d, nm) | 66 ± 0.93 | 75.1 ± 0.75 |
| ζ-potential (mV) | −4.28 ± 0.82 | −3.89 ± 0.5 |

To construct targeted LNPs containing siRNA, which are referred to herein as "TsiLNPs", ASSET and RIg were sequentially added in equimolar amounts to previously described siRNA-loaded LNPs (1). To verify TsiLNPs assembly, the carriers' components were tested by Western blot and LNPs purification was followed by high cutoff (1 MDa) Dialysis (FIG. 2A). ASSET was shown to mediate siLNPs coating by RIg with high efficiency of ~98%. This is in contrast to the inefficiency of carbodiimide-mediated chemical conjugation (<0.5%) (FIG. 6D and Table 2, herein below).

TABLE 2

|  | LNP yield | IgG incorporation | RIg $K_d$ (nM) tested by ELISA |
| --- | --- | --- | --- |
| ccTsiLNPs | 23.5% ± 0.05 | 0.06% ± 0.024 | 1.08 ± 0.049 |
| TsiLNPs | 94.9% ± 0.06 | 98.3% ± 0.016 | 0.24 ± 0.007 |

Moreover, RIg bound to the LNP by ASSET maintained its high affinity (Kd ~0.24 nM), compared to RIg chemically conjugated to LNPs (ccTsiLNPs), which only bound with Kd ~1.08 nM, a 4.5-fold loss in activity, as assayed by ELISA (FIG. 6E and Table 2).

Next, the present inventors tested if TsiLNPs bind to cells bearing the targeted receptor. ASSET-containing LNPs incubated with an LFA-1 RIg were selectively taken up by the LFA-1+ mouse T cell lymphoma cell line TK1. Moreover, incubation of TK1 cells with ASSET LNPs without any antibody (FIG. 2B) or in the absence of ASSET (FIG. 6C) did not result in LNPs binding. To test TsiLNPs versatility, particle uptake was tested in mouse macrophage RAW264.7 cells. RAW264.7 efficiently took up TsiLNPs having a CD44 RIg, detected by both mCherry and siCy5, but not TsiLNPs incubated with irrelevant CD34 RIg (FIG. 2C).

Figure 2D:
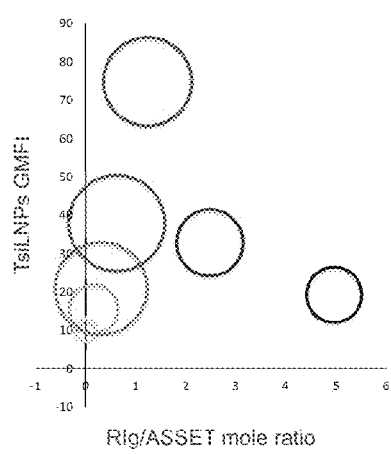

Moreover, uptake of LFA-1 TsiLNPs into TK1 cells was optimal when TsiLNPs were produced using a 1:1 ASSET:RIg ratio (FIG. 2D). These results, together with the complete binding efficiency, suggest that all the added RIgs each bound to one anchored ASSET molecule. This efficient binding to the LNPs meant that a purification step to remove unbound antibodies, which is needed after chemical conjugation and typically involves gel filtration with large losses, was not required.

Figure 2E:
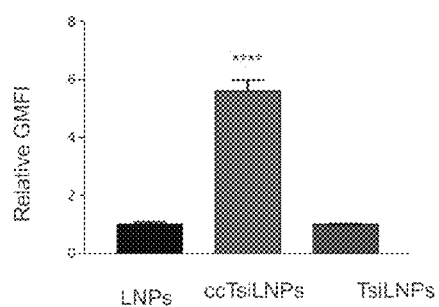

Another important difference between ASSET-bound and chemically conjugated RIg is that ASSET binding occurs via the Fc domain, potentially blocking binding to FcRs on scavenger cells, while chemical conjugation would leave most Fc domains exposed, making conjugated LNPs vulnerable to clearance by Fc-receptor-expressing scavenger cells. To assess FcR recognition, the binding of CD34 TsiLNPs and ccTsiLNPs to rat FcR transiently expressed in HEK293T cells was compared. CD34 TsiLNPs did not bind, but the ccTsiLNPs did (FIGS. 2E, 6F and Table 2). Thus, antibodies bound to TsiLNPs escape FcR recognition.

The present inventors next examined whether TsiLNPs are selectively taken up and cause gene knockdown in targeted cells in vivo after intravenous injection. They chose as targets ordinarily hard-to-transfect lymphocytes, which were previously targeted using ccTsiLNPs (1). CD4 TsiLNPs encapsulating Cy5-conjugated siRNAs administration exhibit specific uptake by blood CD4+ lymphocytes (FIG. 3A). CD4 TsiLNPs incorporating CD45 siRNAs were injected iv and 5 days later CD45 expression was measured in inguinal lymph node CD4+ lymphocytes by flow cytometry (FIG. 3B). In agreement with previous results using ccTsiLNPs, ~30% of CD4+ lymphocytes exhibited CD45 silencing of ~60% (FIG. 3C). Thus, the TsiLNP platform was able to achieve comparable specific silencing as we previously achieved with ccTsiLNP in CD4+ T cells (1). The advantage of the new platform over the old was that this efficacy was achieved with negligible calibration using two orders of magnitude less primary antibody.

To assess the versatility of the ASSET platform, the present inventors next tested whether they could alter which cells were targeted by a simple RIg switch. Uptake of TsiLNPs encapsulating Cy5-conjugated siRNAs incubated with CD3, CD4, β7 integrin, and CD25 antibodies (FIG. 3D) was compared. (37 integrin (Itgb7) is expressed on most T- and B-lymphocytes and CD25 is only expressed brightly on regulatory T cells and less brightly on activated T cells. CD3 TsiLNPs were taken up by both CD4+ and CD4−CD3+ lymphocytes, but not by CD3− cells. CD4 TsiLNPs were uniformly taken up by CD4+ T cells, but not by CD4−CD3+T lymphocytes or CD3− cells. Itgb7 TsiLNPs were taken up by a subset of both CD3+ and CD3− cells, as expected based on its expression by both T and B lymphocytes. CD25 TsiLNP uptake was restricted to the small population of CD25+CD4+ T cells. Thus, simply switching the RIg used for targeting, directs LNP in vivo uptake into cell surface receptor-defined subsets of lymphocytes with precision.

Figure 4I:
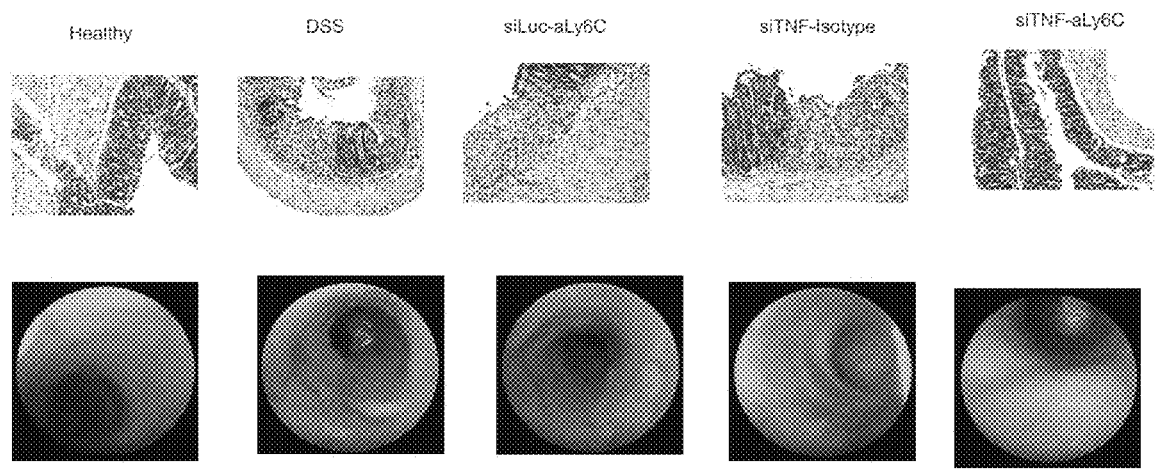

Next the potential therapeutic utility of TsiLNPs was tested. Because secretion of TNFα by intestinal macrophages plays a major role in Inflammatory Bowel Disease (IBD), reducing TNFα secretion in the gut should provide protection in an animal model of IBD (9). An RIg to Ly6C, (a marker of mouse circulating monocytes and inflammatory tissue macrophages (10)) was used for targeting. First, it was determined whether Ly6C TsiLNPs could knock down TNF, the gene encoding TNFα, in the RAW 267 mouse macrophage cell line in vitro (FIG. 4A). Indeed TNF mRNA, assessed by qRT-PCR relative to GAPDH, was reduced to 5.8%. It was next investigated whether intravenously injected TsiLNPs produced with Cy5-labeled siRNAs and αLy6C were taken up by Ly6C+ blood monocytes (FIGS. 4B, C). Indeed, Ly6C+ blood mononuclear cells were Cy5+ in mice treated with Ly6C TsilLNPs, but not with isotype TsilLNPs. Oral administration of the detergent dioctyl sodium sulfosuccinate (DSS) causes colitis in mice and is used as a model of IBD (9). To assess the therapeutic efficacy of TsiLNPs in the DSS colitis model, Ly6C or isotype control antibody TsiLNPs encapsulating TNFα siRNAs were administered intravenously 3, 5 and 7 days after giving DSS. TNFα knockdown and colitis severity were assessed on day 8. Ly6C-TsiLNPs reduced TNFα protein in the large intestine by ~3-fold (FIG. 4D), even below its level in non-inflamed gut. IL-6 expression in the gut, an indicator of inflammation, was also drastically reduced to its baseline levels in healthy mice (FIG. 4E). DSS colitis leads to profound weight loss, a shortening of the inflamed colon and erythema, swelling and inflammatory infiltration of the colon. All of these disease signs were significantly and dramatically reduced in mice receiving Ly6C TsiLNPs bearing TNF siRNAs (FIGS. 4F-H). In contrast there was minimal or no protection by TsiLNPs assembled with isotype control RIg or Luc siRNA. Thus, targeted delivery of TNF siRNAs to Ly6C+ macrophages by TsiLNPs provided protection from DSS colitis.

To test TsiLNP application for cancer therapy, the present inventors used a model of disseminated bone marrow MCL generated by intravenous injection of a human MCL cell line into immunodeficient mice. Human CD29 RIg was chosen to target these lymphoma cells, and PLK1 siRNAs were used to cause G2/M cell cycle arrest and then cell death. After verifying that αCD29 TsiLNP knocked down PLK1 in Granta-519 cells in vitro (FIG. 7A) and caused cell cycle arrest (FIG. 7B), its effect on survival of mice bearing MCL tumors was investigated. αCD29 or isotype control antibody TsiLNP encapsulating PLK1 siRNAs were administered intravenously every 3 days beginning 5 days after tumor cell injection (FIG. 7C). Mock-treated mice and mice that were treated with TsiLNP assembled with isotype control RIg had median survival of 24 and 28 days, respectively, while mice treated with αCD29 TsiLNP showed prolong survival for a median of 46 days.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An immunoparticle comprising a lipidated secondary antibody comprising a secondary antibody attached via a linker to a lipidated peptide comprising an inner membrane lipidation signal, said lipidated secondary antibody is non-covalently attached to an outer surface of a synthetic lipid-based nanoparticle comprising synthetic lipids via said lipidated peptide, and attached to a primary antibody via an antigen recognition domain of said secondary antibody, wherein said secondary antibody has specificity for said primary antibody.

2. The immunoparticle of claim 1, wherein said primary antibody is a humanized or human primary antibody.

3. The immunoparticle of claim 1, wherein said immunoparticle is loaded with a diagnostic or a therapeutic agent.

4. The immunoparticle of claim 1, wherein said therapeutic agent is a polynucleotide agent.

5. The immunoparticle of claim 1, wherein said primary antibody and said secondary antibody are of different antibody classes or antibody isotypes.

6. The immunoparticle of claim 1, wherein said primary antibody and said secondary antibody are selected from the group consisting of IgG1, IgG2 and IgG4.

7. The immunoparticle of claim 1, wherein said lipid-based nanoparticle comprises a charged external surface.

8. The immunoparticle of claim 1, wherein said lipid-based nanoparticle comprises cationic lipids.

9. The immunoparticle of claim 1, wherein said primary antibody comprises an Fc region and said secondary antibody binds said Fc region of said primary antibody.

10. The immunoparticle of claim 4, wherein said polynucleotide agent is an siRNA.

11. The immunoparticle of claim 1, wherein said lipidated peptide comprises SEQ ID NO: 13.

12. The immunoparticle of claim 1, wherein said lipidated peptide consists of SEQ ID NO: 13.

* * * * *